US006476198B1

(12) United States Patent
Kang

(10) Patent No.: US 6,476,198 B1
(45) Date of Patent: Nov. 5, 2002

(54) MULTISPECIFIC AND MULTIVALENT ANTIGEN-BINDING POLYPEPTIDE MOLECULES

(75) Inventor: Angray Singh Kang, Carlsbad, CA (US)

(73) Assignee: The Scripps Research Institute, La Jolla, CA (US)

( * ) Notice: Subject to any disclaimer, the term of this patent is extended or adjusted under 35 U.S.C. 154(b) by 1258 days.

(21) Appl. No.: 08/495,209

(22) Filed: Jun. 27, 1995

Related U.S. Application Data

(63) Continuation-in-part of application No. 08/092,111, filed on Jul. 13, 1993, now abandoned.

(51) Int. Cl.$^7$ ...................... C07K 16/00; A61K 39/395
(52) U.S. Cl. ................... 530/387.3; 424/136.1
(58) Field of Search ........................ 530/387.3, 388.1, 530/387.1; 424/136.1

(56) References Cited

U.S. PATENT DOCUMENTS

| 5,258,498 A | * 11/1993 | Huston et al. ............ 530/387.3 |
| 5,292,668 A | * 3/1994 | Paulus et al. ............. 530/387.3 |

FOREIGN PATENT DOCUMENTS

| WO | 88/09344 | * 12/1988 |

OTHER PUBLICATIONS

George Et Al., J. Cell. Biochem., 1991, 15E:127, Abstract N206.*
Traunecker et al., EMBO J., 1991, 10:3655.*
Knox, et al., "Observations on the Effect of Chimeric Anti–CD4 Monoclonal Antibody in Patients with Mycosis Fungoides", *Blood*, 77: 20–30 (1991).
Barbas, et al., "Assembly of Combinatorial Antibody Libraries on Phage Surfaces: The Gene III Site", *PNAS, USA*, 88: 7978–7982 (1991).
Wels, et al., "Construction, Bacterial Expression and Characterization of a Bifunctional Single–Chain Antibody–Phosphatase Fusion Protein Targeted to the Human ERBB–2 Receptor", *Bio/Technology*, 10: 1128–1132 (1992).
Stemmer, et al., "Selection of an Active Single Chain Fv Antibody From a Protein Linker Library Prepared by Enzymatic Inverse PCR", *Bio Techniques*, 14: 256–265 (1993).
Skerra, "Bacterial Expression of Immunoglobulin Fragments", *Current Opinion in Immunology*, 5: 256–262 (1993).
Pack, et al, "Miniantibodies: Use of Amphipathic Helices to Produce Functional, Flexibly Linked Dimeric Fv Fragments with High Avidity in *Escherichia coli*", *Biochemistry*, 31: 1579–1584 (1992).
Leung, et al., "A Method for Random Mutagenesis of a Defined DNA Segment Using a Modified Polymerase Chain Reaction", *J. Methods Cell Molecular Biol.*, 1: 11–15 (1989).
Kang, et al., "Linkage of Recognition and Replication Functions by Assembling Combinatorial Antibody Fab Libraries Along Phage Surfaces", *PNAS, USA*, 88: 4363–4366 (1991).
Sandhu, "Protein Engineering of Antibodies", *Crit. Reviews in Biotech.*, 12: 437–462 (1992).

* cited by examiner

Primary Examiner—David Saunders
(74) Attorney, Agent, or Firm—Thomas Fitting; Emily Holmes; Thomas E. Northrup

(57) ABSTRACT

The present invention relates to multispecific and multivalent antigen-binding polypeptides and methods for producing them.

9 Claims, No Drawings

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 21 amino acids

```
            (B) TYPE: amino acid
            (D) TOPOLOGY: linear (ii) MOLECULE TYPE: protein (xi) SEQUENCE DESCRIPTION: SEQ ID NO:1:

Met Lys Tyr Leu Leu Pro Thr Ala Ala Ala Gly Leu Leu Leu Leu Ala
1               5                   10                  15

Ala Gln Pro Ala Met
            20

(2) INFORMATION FOR SEQ ID NO:2:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Tyr Leu Leu Pro Thr Ala Ala Ala Gly Leu Leu Leu Leu Ala
1               5                   10                  15

Ala Gln Pro Ala Gln Pro Ala Met Ala
            20                  25

(2) INFORMATION FOR SEQ ID NO:3:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:3:

Met Lys Ser Leu Ile Thr Pro Ile Ala Ala Gly Leu Leu Leu Ala Phe
1               5                   10                  15

Ser Gln Tyr Ser Leu Ala
            20

(2) INFORMATION FOR SEQ ID NO:4:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile
            20                  25

(2) INFORMATION FOR SEQ ID NO:5:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:5:
```

```
Met Met Lys Arg Asn Ile Leu Ala Val Ile Val Pro Ala Leu Leu Val
1               5                   10                  15

Ala Gly Thr Ala Asn Ala Ala Glu
            20
```

(2) INFORMATION FOR SEQ ID NO:6:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Gln Ser Thr Ile Ala Leu Ala Leu Leu Pro Leu Leu Phe Thr
1               5                   10                  15

Pro Val Thr Lys Ala Arg Thr
            20
```

(2) INFORMATION FOR SEQ ID NO:7:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:7:

```
Met Ser Ile Gln His Phe Arg Val Ala Leu Ile Pro Phe Phe Ala Ala
1               5                   10                  15

Phe Cys Leu Pro Val Phe Ala His Pro
            20                  25
```

(2) INFORMATION FOR SEQ ID NO:8:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:8:

```
Met Met Ile Thr Leu Arg Lys Leu Pro Leu Ala Val Ala Val Ala Ala
1               5                   10                  15

Gly Val Met Ser Ala Gln Ala Met Ala Val Asp
            20                  25
```

(2) INFORMATION FOR SEQ ID NO:9:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:9:

```
Met Lys Ala Thr Lys Leu Val Leu Gly Ala Val Ile Leu Gly Ser Thr
1               5                   10                  15

Leu Leu Ala Gly Cys Ser
            20
```

(2) INFORMATION FOR SEQ ID NO:10:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Lys Ser Leu Val Leu Lys Ala Ser Val Ala Val Ala Thr Leu
1               5                   10                  15

Val Pro Met Leu Ser Phe Ala
            20

(2) INFORMATION FOR SEQ ID NO:11:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:11:

Met Lys Lys Leu Leu Phe Ala Ile Pro Leu Val Val Pro Phe Tyr Ser
1               5                   10                  15

His Ser (2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:12:

AAUCUUGGAG GCUUUUUUAU GGUUCGUUCU                                    30

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:13:

UAACUAAGGA UGAAAUGCAU GUCUAAGACA                                    30

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:14:

UCCUAGGAGG UUUGACCUAU GCGAGCUUUU                                            30

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:15:

AUGUACUAAG GAGGUUGUAU GGAACAACGC                                            30

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

CAGATCCAGT TGCTCCAGTC TGGACC                                                26

(2) INFORMATION FOR SEQ ID NO:17:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

CTGGGTCATC TGGAGCTCGG CCAGTGGATA GACAGATGGG GGTGTCGTTT TGGC                 54

(2) INFORMATION FOR SEQ ID NO:18:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:18:

Val Thr Val Ser Ser Ala Lys Thr Thr Pro Ser Val Tyr Pro Leu
1               5                  10                 15

Ala Glu Leu (2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

TCTACTGAGC TCGTGATGAC CCAAACTCCA                                      30

(2) INFORMATION FOR SEQ ID NO:20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GCGCCGTCTA GAATTAACAC TCATTCCTGT TGAA                                 34

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

ATTAACCCTC ACTAAAG                                                    17

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

AATATCGACG TCACCTCCAC ACTCATTCCT GTTGAA                                36

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

TCCTGGGAAA GATTGTAATA CGAC                                             24

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

CATCTGGATA TCCGCCAGGG GGAAGACGGA                                       30

(2) INFORMATION FOR SEQ ID NO:25:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

AACCTGGGAT CCGCCCCCAC ACTCTCCCCT GTTGAAGAAG CTCTT                      45

(2) INFORMATION FOR SEQ ID NO:26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

TGTGGGGGCG GATCCCAGGT TCAGCTGGTG CAGTCTGGAG GAGGA                      45

(2) INFORMATION FOR SEQ ID NO:27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

TATAGGATCC TATTATCTTG TGATCTGCAG CTTTG                        35

(2) INFORMATION FOR SEQ ID NO:28:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

GAGTGTGGAG GGGGTTCTGA TATCCAGATG ACACAGTCTC CT               42

(2) INFORMATION FOR SEQ ID NO:29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

CTGAACCTGA GATCCCCCGA AGATGAAGAC AGACGGCGCC GCCACAGT          48

(2) INFORMATION FOR SEQ ID NO:30:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

GTCTTCATCT TCGGGGGATC TCAGGTTCAG CTGGTGGAGT CT               42

(2) INFORMATION FOR SEQ ID NO:31:

(i) SEQUENCE CHARACTERISTICS:
           (A) LENGTH: 48 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:31:

CATCTGGATA TCAGAACCCC CTCCACACTC TCCCCTGTTG AAGCTCTT                48

(2) INFORMATION FOR SEQ ID NO:32:

(i) SEQUENCE CHARACTERISTICS:
           (A) LENGTH: 48 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

CATCTGGATA TCAGAACCCC CTCCACACTC TCCCCTGTTG AAGCTCTT                48

(2) INFORMATION FOR SEQ ID NO:33:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

CCCCCTGGCG GGGGATATCC AGATGACACA GTCTCC                            36

(2) INFORMATION FOR SEQ ID NO:34:

(i) SEQUENCE CHARACTERISTICS:
           (A) LENGTH: 41 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

GCAGCTTGGG CTGTGTGATC TGCAGCTTTG TTCCCTGTCC G                      41

(2) INFORMATION FOR SEQ ID NO:35:

(i) SEQUENCE CHARACTERISTICS:
           (A) LENGTH: 35 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

AGAATGCGGC CGCCACCATG GAATGGAGCT GGGTC                                   35

(2) INFORMATION FOR SEQ ID NO:36:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

CTGGATATCC CCCGCCAGGG GGAAGACGGA TGGGCCC                                 37

(2) INFORMATION FOR SEQ ID NO:37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

AAGCTGCAGA TCACACAGCC CAAGGCTGCC CCCTCGGTC                               39

(2) INFORMATION FOR SEQ ID NO:38:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

AAATGCGGCC GCTTATGAAC ATTCCGTAGG GGCAACTGTC TTCTCC                       46

MULTISPECIFIC AND MULTIVALENT ANTIGEN-BINDING POLYPEPTIDE MOLECULES

RELATED APPLICATIONS

This application is a continuation-in-part of U.S. application Ser. No. 08/092,111, filed on Jul. 13, 1993 and now abandoned.

TECHNICAL FIELD

The present invention relates to multispecific and multivalent antigen-binding polypeptides and methods for producing them.

BACKGROUND

The ability to target and activate cytotoxic lymphocytes opens the way to utilize natural effector functions to treat cancer, auto-immune disorders and infectious diseases. See, Segal et al., *Chem. Immunology*, Ed. Ishizaka et al., 47:179–213 (1989). Bispecific antibodies allow this linking of target cell to the effector cell. However, the bispecific antibodies generated so far have two major drawbacks.

Firstly, the specificities against human antigens are predominantly encoded by rodent antibodies and would result in a human anti-murine antibody (HAMA) response in repeated or prolonged use. Although the specificity problem has partially been overcome by forming chimeric (Knox, et al., *Blood*, 77:20, 1991); Shaw, et al., *J. Biol. Response Med.*, 7:204, (1988); and Oudin, et al., *Proc. Natl. Acad. Sci. USA*, 63:266, (1971)) and humanized (Hale, et al., *Lancet*, 2:1394, (1988)) antibodies, the problem of immunogenicity still persists. Advances in applying combinatorial antibody repertoire cloning for the generation of human monoclonal antibodies provides a source of human derived variable, framework and constant regions thus theoretically avoiding a HAMA response. This approach works well when an immune source for the desired specificity is available, but is of limited value in the search for antibodies which specifically bind human cell surface molecules.

Secondly, current methods for producing bispecific molecules rely on either chemical cross linking or heterohybridoma (quadroma) formation. The former approach results in a heteroconjugates resulting in preparations that vary from batch to batch in terms of composition and consequently potency. The latter approach involves fusing the two hybridoma cell lines producing the desired antibodies, giving rise to a quadroma cell encoding and expressing all the H and L chains. The desired H and L chain combination for the bispecific antibody is usually only 15% of the total antibody and is difficult to isolate from the closely related pool of antibodies as described by Milstein et al., *Nature*, 305:537 (1983).

Ideally human variable regions conferring the desired specificities should be used to construct a single molecule containing both the specificities as the major if not only product. Alternatively, variable regions conferring the desired specificities should be used to construct two polypeptide molecules containing immunologically distinct constant region domains wherein the majority of the two polypeptide molecules are linked by disulphide bonding. Such molecules would avoid the HAMA response while facilitating production of a homogeneous product for characterization and clinical evaluation.

The ability to PCR amplify, directionally clone and express antibody variable regions from cDNA has allowed hybridoma technology to be bypassed. Diverse high affinity antibodies have been generated to hapten, virus particles and protein antigens, thereby recapitulating functional molecules appearing during the natural immune response in animals and in humans. See, for example, Skerra et al., *Science*, 240:1038–1041 (1988); Better et al., *Science*, 240:1041–1043 (1988); Orlandi et al., *Proc. Natl. Acad. Sci., USA*, 86:3833–3837 (1989); Kang et al., *Proc. Natl. Acad. Sci., USA*, 88:4363–4366 (1991); and Barbas et al., *Proc. Natl. Acad. Sci.. USA*, 88:7978–7982 (1991). Marks et al., *J. Mol. Biol.*, 222:581–597 (1991) demonstrated that active single chain antibody Fv fragments with affinity constants in the range of $10^6$–$10^7$ M-1 against a hapten or a small number of epitopes on a protein can be obtained directly from non-immune combinatorial immunoglobulin libraries. More recently, a combinatorial library approach was used to select monoclonal antibodies from non-immune mice and subsequently affinity mature the specificities, thereby establishing the principles of (i) accessing naive combinatorial antibody libraries for predefined specificities and (ii) increasing the affinity of the selected antibodies binding sites by random mutagenesis. See, Gram et al., *Proc. Natl. Acad. Sci., USA*, 89:3576–3580 (1992).

In addition, large libraries of antibody Fab fragments have been displayed on the surface of phage. See, for example, Kang et al., *Proc. Natl. Acad. Sci., USA*, 88:4363–4366 (1991); Hoogenboom et al., *Nuc. Acids. Res.*, 19:4133–4137 (1991); Burton et al., *Proc. Natl. Acad. Sci., USA*, 88:10134–10137 (1991); Griffiths et al., *EMBO J.*, 12:725–734 (1993); and Soderlind et al., *Bio/Technology*, 11:503–507 (1993). In essence, the antigen recognition unit has been linked to instructions for its production. An iterative process of mutation followed by selection has also been developed allowing for the rapid generation of specific antibodies from germ line sequences as describe by Gram et al., supra.

The B cell immune response to an antigen can be viewed to occur in two stages. The initial stage generates low affinity antibodies mostly of the IgM isotype from an existing pool of the B-cell repertoire available at the time of immunization. The second stage which is driven by antigen stimulation produces high affinity antibodies predominantly of the IgG isotype, starting with the VH and VL genes selected in the primary response. The predominant mechanism for affinity maturation is hypermutation of variable region genes (and possibly gene conversion) followed by selection of those cells which produce antibodies of the highest affinity. In its simplest form, the initial stage of the immune response can be recreated in vitro by generating a combinatorial library of PCR amplified IgM/G and light chains from the bone marrow of adults. This is a close approximation to the naive, unselected repertoire, since the majority of the B cells in the bone marrow expressing IgM/G chains have not been subjected to tolerance and antigen selection, and should therefore represent all the combinatorial diversity of immunoglobulin V-regions. See, Decker et al., *J. Immunol.*, 146:350–361 (1991). The phagemid pComb8 facilitates the display of multiple copies of the single chain antibody along the phage surface permitting the access to low affinity antibodies as described by Kang et al., supra and Gram et al., supra. Hence, specific VH and VL pairs could possibly be enriched from a diverse naive repertoire.

The second stage of the immune response in vivo involves affinity maturation of the selected specificities by mutation and selection. An efficient way to generate random mutations is by an error-prone replication mechanism, either by targeting the mutations to the antibody binding sites by error-prone PCR as described by Leung et al., *J. Methods Cell Molecular Biol.*, 1:1–15 (1989), or by passaging the phagemid carrying the genetic information for the antigen binding domain through an *E.coli* mutD strain, in which the spontaneous mutation frequency is 103 to 105 times higher than in a wild-type strain as described by Fowler et al., *J. Bacteriol.*, 167:130–137 (1986). Selected VH and VL pairs could be subjected to error prone PCR (also gene conversion by PCR is feasible) and the resulting products cloned into phagemid pComb3 which facilitates the display of a single copy of the mutant single chain Fv, such low level of display permits the isolation of the highest affinity molecules.

Variations of single chain bispecific molecules have been constructed in bacteria by linking two single chain heavy and light chain variable domains (sFv) with a synthetic linker. See, for example, Wels et al., *Bio/Technology*, 10:1128–1132 (1992); Stemmer et al., *BioTechniques*, 14:256–265 (1993); Goshorn et al., *Cancer Res.*, 53:2123–2127 (1993); and Bos et al., *Biotherapy*, 5:187–199 (1992). The molecules generated, however, are incorrectly folded and on denaturing and refolding result in very low yield. This may be intrinsically due to expressing both the specificities as a single protein giving rise to inter- and intra-molecular heterodimers. Earlier studies have shown that vector-expressed heavy and light chains that were secreted into the periplasmic space assembled with a disulfide bond linking the constant domain. See, Kang et al., supra and Barbas et al., supra.

Bispecific molecules have also been shown to assemble as dimers. Pack et al., *Biochem.*, 31:1579–1584 (1992) have described one such dimeric antibody produced in *E. coli* that is based on a sFv fragment with a flexible hinge region from mouse IgG3 and an amphipathic helix fused to the carboxy terminus of the antibody fragment. For reviews of protein engineering of antibodies including bivalent and bispecific antibodies see Skerra, *Current Opinion in Immunol.*, 5:256–262 (1993) and Sandhu, *Crit. Reviews Biotech.*, 12:437–462 (1992). While molecules exist that have both bivalent and bispecific properties, these molecules have undesirable properties of being expressed and purified in low quantities, unstable in a dimer conformation, of having regions that would induce an immunogenic response against the molecule or having effector and complement activation functions mediated by the presence of Fc.

Methods have now been discovered to produce bispecific multivalent polypeptides derived from human antibodies thus eliminating an immune response when used in immunotherapy. The bispecific multivalent polypeptides can be expressed and purified to near homogeneity by sequential purification.

BRIEF SUMMARY OF THE INVENTION

Methods have now been discovered that result in the production of molecules that exist in stable multimeric conformations having more than one antigen-binding specificity while lacking undesirable effector or complement activation functions. Because of the multivalent conformations, the compositions of this invention are not destroyed by the body and circulate as functional molecules much like intact immunoglobulins for longer periods of time than their Fab counterparts. The methods of this invention provide for the formation of multimeric compositions in functional form in *E. coli* and mammalian cells. In addition, the stable multimeric polypeptide molecules exhibit increased avidity over the monomeric antigen binding sites due to the functional folding of the variable domains in the compositions to form two ligand or antigen binding sites. The methods of this invention are useful for generating compositions that have a predetermined immunospecificity that bind to target molecules with increased avidity.

The present invention can be advantageously applied to the production of multivalent molecules of predetermined specificity, i.e., it can be used to produce antibodies, T-cell receptors and the like that bind a preselected ligand.

In one embodiment, the present invention contemplates a composition comprising a bivalent polypeptide having an amino acid residue sequence according to the formula V—X—V, wherein V is an antigen binding site, and X is an amino acid residue sequence of from about 5 to about 120 amino acid residues. In preferred embodiments, X is an immunoglobulin constant domain selected from the group consisting of $C_H$ and $C_L$. In one aspect of this embodiment, the $C_L$ domain is selected from the group consisting of $C_\kappa$ or $C_\lambda$. In another aspect of this embodiment, the two antigen binding sites can each have the same or different antigen binding specificities, thereby providing monospecific or bispecific binding reactivities, respectively. A preferred antigen binding site is a polypeptide comprising an immunoglobulin variable heavy and light chain domain fusion selected from the group consisting of $V_H/V_L$ and $V_L/V_H$, wherein $V_H$ is the immunoglobulin variable heavy chain domain and $V_L$ is the immunoglobulin variable light chain domain.

In a related embodiment, the invention contemplates a composition comprising a monovalent polypeptide having an amino acid residue sequence according to the formula V—C, wherein V is an antigen binding site, and C is an immunoglobulin constant domain amino acid residue sequence selected from the group consisting of $C_H$ and $C_L$. In one aspect of this embodiment, the $C_L$ domain is selected from the group consisting of $C_\kappa$ or $C_\lambda$. In preferred embodiments, the antigen binding site is a polypeptide comprised of an immunoglobulin variable heavy and light chain domain fusion selected from the group consisting of $V_H/V_L$ and $V_L/V_H$.

Also contemplated are polypeptide compositions comprising two or more polypeptides of the present invention operatively linked by disulfide bridges between the immunoglobulin constant domain of each polypeptide, thereby forming multimeric proteins having multiple valencies and antigen-binding specificities. In this embodiment, the immunoglobulin constant region domain is selected from the group consisting of $C_H$ and $C_L$ wherein the $C_L$ domain is selected from the group consisting of $C_\kappa$ or $C_\lambda$, thereby providing a means of sequential purification based upon the different immunological properties of the constant region domains.

Also described are DNA vectors for producing a polypeptide composition of the present invention, and methods of preparing and using the polypeptide compositions.

DETAILED DESCRIPTION OF THE INVENTION

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 C.F.R. 1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine.

Nucleic Acid: A polymer of nucleotides, either single or double stranded.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention,include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: A double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it non-randomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

DNA Homolog: A nucleic acid having a preselected conserved nucleotide sequence and a sequence coding for a receptor capable of binding a preselected ligand.

Recombinant DNA (rDNA) molecule: A DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules of the compositions of this invention, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and Fv.

Immunoglobulin Constant Region: Immunoglobulin constant regions are those structural portions of an antibody molecule comprising amino acid residue sequences within a given isotype which may contain conservative substitutions therein. Exemplary heavy chain immunoglobulin constant regions are those portions of an immunoglobulin molecule known in the art as CH1, CH2, CH3, CH4 and CH5. An exemplary light chain immunoglobulin constant region is that portion of an immunoglobulin molecule known in the art as $C_L$.

Conservative Substitution: The term conservative substitution as used herein denotes the replacement of an amino acid residue by another, biologically similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term conservative substitution also includes the use of a substituted amino acid in place of an unsubstituted parent amino acid provided that molecules having the substituted polypeptide also have the same function.

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof. Alternatively, an antibody combining site is known as an antigen binding site.

Valency: The term valency refers to the number of potential antigen binding sites in a polypeptide. A polypeptide may be monovalent and contain one antigen binding site or a polypeptide may be bivalent and contain two antigen binding sites. Additionally, a polypeptide may be tetravalent and contain four antigen binding sites. Each antigen binding site specifically binds one antigen. When a polypeptide comprises more than one antigen binding site, each antigen binding site may specifically bind the same or different antigens. Thus, a polypeptide may contain a plurality of antigen binding sites and therefore be multivalent and a polypeptide may specifically bind the same or different antigens.

Specificity: The term specificity refers to the number of potential antigen binding sites which immunoreact with (specifically bind) a given antigen in a polypeptide. The polypeptide may be a single polypeptide or may be two or more polypeptides joined by disulfide bonding. A polypeptide may be monospecific and contain one or more antigen binding sites which specifically bind an antigen or a polypeptide may be bispecific and contain two or more antigen binding sites which specifically bind two immunologically distinct antigens. Thus, a polypeptide may contain a plurality of antigen binding sites which specifically bind the same or different antigens.

Multimeric: A polypeptide comprising more than one polypeptide. A multimer may be dimeric and contain two polypeptides and a multimer may be trimeric and contain three polypeptides. Multimers may be homomeric and contain two or more identical polypeptides or a multimer may be heteromeric and contain two or more nonidentical polypeptides.

Single Chain Antibody: The phrase single chain antibody refers to a single polypeptide comprising one or more antigen binding sites.

Polypeptide: The phrase polypeptide refers to a molecule comprising amino acid residues which do not contain linkages other than amide linkages between adjacent amino acid residues.

Immunologically Distinct: The phrase immunologically distinct refers to the ability to distinguish between two polypeptides on the ability of an antibody to specifically bind one of the polypeptides and not specifically bind the other polypeptide.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Stop Codon: Any of three codons that do not code for an amino acid, but instead cause termination of protein synthesis. They are UAG, UAA and UGA and are also referred to as a nonsense or termination codon.

Leader Polypeptide: A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame: Particular sequence of contiguous nucleotide triplets (codons) employed in translation. The reading frame depends on the location of the translation initiation codon.

B. DNA Expression Vectors

A vector of the present invention is a recombinant DNA (rDNA) molecule adapted for receiving and expressing translatable DNA sequences in the form of a polypeptide of this invention. The vector comprises a cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the that portion of the polypeptide which is expressed when polypeptides of this invention are expressed on the surface of phage. The vector preferably includes DNA expression control sequences for expressing the fusion polypeptide that is produced when an insert translatable DNA sequence (insert DNA) is directionally inserted into the vector via the sequence of nucleotides adapted for directional ligation.

An expression vector is characterized as being capable of expressing, in a compatible host, a structural gene product such as a polypeptide of the present invention.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked.

As used herein with regard to DNA sequences or segments, the phrase "operatively linked" means the sequences or segments have been covalently joined, preferably by conventional phosphodiester bonds, into one strand of DNA, whether in single or double stranded form.

The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In a preferred embodiment, the vector utilized includes a prokaryotic replicon i.e., a DNA sequence having the ability to direct autonomous replication and maintenance of the recombinant DNA molecule extra chromosomally in a prokaryotic host cell, such as a bacterial host cell, transformed therewith. Such replicons are well known in the art. In addition, those embodiments that include a prokaryotic replicon also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

In another preferred embodiment, the vector utilized includes a eukaryotic replicon i.e., a DNA sequence having the ability to direct autonomous replication and maintenance of the recombinant DNA molecule extra chromosomally in a eukaryotic host cell, such as a mammalian or yeast host cell, transformed therewith. Such replicons are well known in the art and include those replicons which carry the SV40 and 2 $\mu$ origins of replication for replication in mammalian cells and yeast, respectively. SV40 replicons require the expression of the SV40 large T antigen to support the transient replication of replicons carrying the SV40 origin of replication. In addition, those embodiments that include a eukaryotic replicon also include a gene whose expression confers a selective advantage, such as drug resistance, to a mammalian host transformed therewith. A typical mammalian drug resistance gene is that which confers resistance to G418. Genes whose expression confer a selective advantage to a mammalian host transformed therewith also include those which encode required amino acids, such as leucine, tryptophan, uracil and histidine. Vectors typically also contain convenient restriction sites for insertion of translatable DNA sequences. Exemplary vectors are the plasmids pSVL, pCH110, pMSG, pBPV and pSVK 3 available from Pharmacia (Piscataway, N.J.); the plasmids pBK-CMV, pBK-RSV, pXT1 pSG5, pRS413, pRS414, pRS415, and pRS416 available from Stratagene (La Jolla, Calif.); the plasmids pYES and pYES2 available from Invitrogen (San Diego, Calif.).

In another embodiment, the vector utilized includes an insect replicon i.e., a DNA sequence having the ability to direct autonomous replication and maintenance of the recombinant DNA molecule extra chromosomally in an insect host cell, such as an Sf9 host cell, transformed therewith. Such replicons are well known in the art. Vectors typically also contain convenient restriction sites for insertion of translatable DNA sequences. Exemplary vectors are the plasmids pMbac and ppbac and the transfer vector pJVP10Z available from Stratagene.(La Jolla, Calif.).

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

A translatable DNA sequence is a linear series of nucleotides that provide an uninterrupted series of at least 8 codons that encode a polypeptide in one reading frame.

An upstream translatable DNA sequence encodes a prokaryotic, eukaryotic or insect secretion signal. The secretion signal is a leader peptide domain of protein that targets the protein to the periplasmic membrane of gram negative bacteria, to the endoplasmic reticulum in mammalian cells or to the secretory pathway of the host insect cell.

A preferred secretion signal is a pelB secretion signal in *E. coli*. The predicted amino acid residue sequences of the secretion signal domain from two pelB gene product variants from *Erwinia carotova* are shown in Table 1 as described by Lei, et al., *Nature,* 331:543–546 (1988). A particularly preferred pelB secretion signal is also shown in Table 1.

The leader sequence of the pelB protein has previously been used as a secretion signal for fusion proteins. Better et al., *Science,* 240:1041–1043 (1988); Sastry et al., *Proc. Natl. Acad. Sci. USA,* 86:5728–5732 (1989); and Mullinax et al., *Proc. Natl. Acad. Sci. USA,* 87:8095–8099 (1990).

Amino acid residue sequences for other secretion signal polypeptide domains from *E. coli* useful in this invention are also listed in Table 1. Oliver, In Neidhard, F. C. (ed.), *Escherichia coli* and *Salmonella Typhimurium,* American Society for Microbiology, Washington, D.C., 1:56–69 (1987).

A translatable DNA sequence encoding the pelB secretion signal having the amino acid residue sequence shown in SEQ ID NO 1 is a preferred DNA sequence for inclusion in a DNA expression vector of this invention.

A downstream translatable DNA sequence may encode antigen-binding site(s) and constant region(s) of the polypeptide(s) as described further herein.

TABLE 1

Leader Sequences

| SEQ ID NO | Type | Amino Acid Residue Sequence |
|---|---|---|
| (1) | pelB[1] | MetLysTyrLeuLeuProThrAlaAlaAlaGlyLeuLeu LeuLeUAlaAlaGlnProAlaMet |
| (2) | pelB[2] | MetLysTyrLeuLeuProThrAlaAlaAlaGlyLeuLeu LeuLeuAlaAlaGlnProAlaGlnProAlaMetAla |
| (3) | pelB[3] | MetLysSerLeuIleThrProIleAlaAlaGlyLeuLeu LeuAlaPheSerGlnTyrSerLeuAla |
| (4) | MalE[4] | MetLysIleLysThrGlyAlaArgIleLeuAlaLeuSer AlaLeuThrThrMetMetPheSerAlaSerAlaLeuAla LysIle |
| (5) | OmpF[4] | MetMetLysArgAsnIleLeuAlaValIleValProAla LeuLeuValAlaGlyThrAlaAsnAlaAlaGlu |
| (6) | PhoA[4] | MetLysGlnSerThrIleAlaLeuAlaLeuLeuProLeu LeuPheThrProValThrLysAlaArgThr |
| (7) | Bla[4] | MetSerIleGlnHisPheArgValAlaLeuIleProPhe PheAlaAlaPheCysLeuProValPheAlaHisPro |
| (8) | LamB4 | MetMetIleThrLeuArgLysLeuProLeuAlaValAla ValAlaAlaGlyValMetSerAlaGlnAlaMetAlaVal Asp |
| (9) | Lpp[4] | MetLysAlaThrLysLeuValLeuGlyAlaValIleLeu GlySerThrLeuLeuAlaGlyCysSer |
| (10) | cpVIII[5] | MetLysLysSerLeuValLeuLysAlaSerValAlaVal AlaThrLeuValProMetLeuSerPheAla |
| (11) | cpIII[6] | MetLysLysLeuLeuPheAlaIleProLeuValValPro PheTyrSerHisSer |

[1]pelB used in this invention
[2]pelB from *Erwinia carotovora* gene
[3]pelB from *Erwinia carotovora* EC 16 gene
[4]leader sequences from *E. coli*
[5]leader sequence for cpVIII
[6]leader sequence for cpIII Exemplary insect cell secretion signals, melittin and human placental alkaline phosphatase, can be found in the transfer vector pJVP10Z (Stratagene).

A cassette in a DNA expression vector of this invention is the region of the vector that forms, upon insertion of a translatable DNA sequence (insert DNA), a sequence of nucleotides capable of expressing, in an appropriate host, a fusion polypeptide of this invention. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli,* the ribosome binding site includes an initiation codon (AUG) and a sequence 3–9 nucleotides long located 3–11 nucleotides upstream from the initiation codon (Shine et al., *Nature,* 254:34 (1975)). The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors:

(i) The degree of complementarity between the SD sequence and 3' end of the 16S tRNA.

(ii) The spacing and possibly the DNA sequence lying between the SD sequence and the AUG (Roberts et al., *Proc. Natl. Acad. Sci. USA,* 76:760 (1979a); Roberts et al., *Proc. Natl. Acad. Sci. USA,* 76:5596 (1979b); Guarente et al., *Science,* 209:1428 (1980); and Guarente et al., *Cell,* 20:543 (1980).) Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold et al., *Annu. Rev. Microbiol.,* 35:365 (1981)). Leader sequences have been shown to influence translation dramatically (Roberts et al., 1979 a, b supra).

(iii) The nucleotide sequence following the AUG, which affects ribosome binding (Taniguchi et al., *J. Mol. Biol.,* 118:533 (1978)).

Useful ribosome binding sites are shown in Table 2 below.

TABLE 2

Ribosome Binding Sites*

| | SEQ ID NO | |
|---|---|---|
| 1. | (12) | 5' AAUCUUGGAGGCUUUUUUAUGGUUCGUUCU 3' |
| 2. | (13) | 5' UAACUAAGGAUGAAAUGCAUGUCUAAGACA 3' |
| 3. | (14) | 5' UCCUAGGAGGUUUGACCUAUGCGAGCUUUU 3' |
| 4. | (15) | 5' AUGUACUAAGGAGGUUGUAUGGAACAACGC 3' |

*Sequences of initiation regions for protein synthesis in four phage mRNA molecules are underlined.
AUG = initiation codon (double underlined)
1. = Phage PhiX174 gene-A protein
2. = Phage QBeta replicase
3. = Phage R17 gene-A protein
4. = Phage lambda gene-cro protein The 3' control sequences define at least one termination (stop) codon in frame with and operatively linked to the downstream translatable DNA sequence. In addition, eukaryotic vectors contain specific nucleotide sequences which provide the necessary signals for polyadenylation of the transcription product derived from the translatable DNA sequence.

Thus, a DNA expression vector of this invention provides a system for cloning translatable DNA sequences into the cassette portion of the vector to produce a cistron capable of expressing a fusion polypeptide of this invention.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication. See, for example, Rasched et al., *Microbiol. Rev.*, 50:401–427 (1986); and Horiguchi, *J. Mol. Biol.*, 188:215–223 (1986).

A preferred filamentous phage origin of replication for use in the present invention is a M13, f1 or fd phage origin of replication. A preferred DNA expression vector is the dicistronic expression vector pCOMB8, described in Example 3.

Insofar as a vector of this invention may be manipulated to contain an insert DNA, thereby having the capacity to express a fusion polypeptide, one embodiment contemplates the previously described vectors containing an insert DNA. Particularly preferred vectors containing antibody genes are described in the Examples.

C. Polypeptides and Polypeptide Compositions

In one embodiment, the present invention contemplates a monovalent polypeptide, and compositions thereof, having an amino acid residue sequence according to the formula V—C, where V is an antigen binding site, and C is an immunoglobulin constant domain amino acid residue sequence selected from the group consisting of $C_H$ and $C_L$.

In a preferred embodiment, the antigen binding site is a polypeptide comprising both the heavy and light chain domains of an immunoglobulin molecule, fused into a single polypeptide to provide a ligand binding capability as is well known in the art. It has been discovered that the orientation of the variable domains of the heavy ($V_H$) and light ($V_L$) chains can vary in either the $V_H$—$V_L$—C or $V_L$—$V_H$—C orientation relative to the constant chain domain (C), when read from amino to carboxy terminus. Thus, in a preferred embodiment, the antigen binding site comprises a polypeptide having an immunoglobulin variable heavy and light chain domain selected from the group consisting of $V_H$—$V_L$ and $V_L$—$V_H$.

In a preferred embodiment, the immunoglobulin constant domain amino acid residue sequences are those polypeptides which comprise the structural portions of an antibody molecule known in the art as CH1, CH2, CH3 and CH4. A particularly preferred heavy chain constant region is CH1 which lacks the effector functions associated with the CH2 region. These effector functions include the binding of the constant region to the Fc receptors, complement fixation and antibody-depedent cell-mediated cytotoxicity. Also preferred are those polypeptides which are known in the art as $C_L$. Preferrred $C_L$ polypeptides are selected from the group consisting of $C_\kappa$ and $C_\lambda$.

The constant and variable regions of a polypeptide can be derived from a variety of sources including mouse, rabbit, rat and human immunoglobulins. Constant and variable regions of a polypeptide which are derived from human immunoglobulins are particularly preferred as they are less immuogenic in humans than polypeptides which are derived from other sources.

As shown herein, the presence of a cysteine residue in the constant domain provides a means for bridging two polypeptides to form a dimeric polypeptide molecule.

Furthermore, insofar as the constant domain can be either a heavy or light chain constant domain ($C_H$ or $C_L$, respectively), a. variety of monovalent polypeptide compositions are contemplated by the present invention. For example, light chain constant domains are capable of disulfide bridging to either another light chain constant domain, or to a heavy chain constant domain. In contrast, a heavy chain constant domain can form two independent disulfide bridges, allowing for the possibility of bridging to both another heavy chain and to a light chain, or to form polymers of heavy chains.

Thus, in another embodiment, the invention contemplates a composition comprising a monovalent polypeptide wherein the constant chain domain C has a cysteine residue capable of forming at least one disulfide bridge, and where the composition comprises at least two monovalent polypeptides covalently linked by said disulfide bridge according to the formula:

In preferred embodiments, the constant chain domain C can be either $C_L$ or $C_H$. Where C is $C_L$, the $C_L$ polypeptide is preferably selected from the group consisting of $C_\kappa$ and $C_\lambda$. Numerous permutations can be used following the above general formula. Particularly preferred is the formula in which C is $C_H$ as follows:

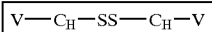

In a related embodiment, additional monovalent polypeptides having the light chain constant regions, $C_L$, can be associated with the above monovalent polypeptide composition. In this embodiment, the polypeptide composition has a structure according to the formula:

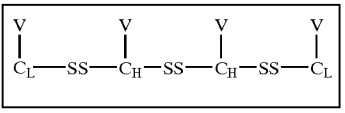

In another embodiment, the invention contemplates a polypeptide composition comprising a monovalent polypeptide as above except where C is $C_L$ having a cysteine residue capable of forming a disulfide bridge, such that the composition contains two monovalent polypeptides covalently linked by said disulfide bridge according to the formula:

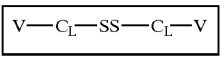

The preparation and use of an exemplary monovalent polypeptide is described further herein, and in the Examples.

In a related embodiment, the present invention describes a bivalent polypeptide, and compositions thereof, where the bivalent polypeptide has an amino acid residue sequence according to the formula V—X—V, where V is an antigen binding site as defined above forming a first and second antigen binding site, and X is an amino acid residue sequence of from about 5 to about 120 amino acid residues.

In one embodiment, the first and second antigen binding sites can each have the same binding specificity. In an alternate embodiment, the first and second antigen binding sites have different binding specificities.

Although a variety of polypeptides can be utilized to link the first and second antigen binding sites, it is particularly preferred where X has a means for reversible linkage to a second polypeptide (monovalent or bivalent). A preferred reversible linkage means is a cysteine residue by virtue of the presence of the available sulfur moiety capable of forming a disulfide bridge with other available sulfur moieties.

In addition, it is particularly preferred that X is an immunoglobulin constant domain selected from the group consisting of the heavy chain constant domain ($C_H$) and the light chain constant domain ($C_L$).

Thus, in another embodiment, the invention contemplates a composition comprising a bivalent polypeptide wherein X is the immunoglobulin heavy chain constant domain ($C_H$) having a cysteine residue capable of forming at least one disulfide bridge, and the composition comprises two bivalent polypeptides covalently linked by said disulfide bridge according to the formula:

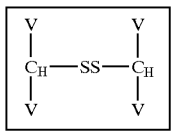

In a related embodiment, the invention contemplates a composition comprising a bivalent polypeptide wherein X is a immunoglobulin heavy chain constant domain ($C_H$) having a cysteine residue capable of forming at least one disulfide bridge and an immunoglobulin light chain constant domain ($C_L$) having a cysteine residue capable of forming at least one disulfide bridge, and the composition comprises two bivalent polypeptides covalently linked by said disulfide bridge according to the formula:

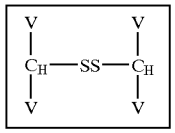

In a related embodiment, additional bivalent polypeptides can be associated with the polypeptide composition wherein the additional bivalent polypeptides have light chain constant regions ($C_L$). The light chain constant regions are selected from the group consisting of $C_\kappa$ and $C_\lambda$. In this embodiment, the polypeptide composition has a structure according to the formula:

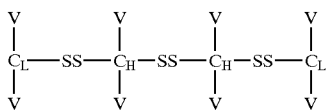

In another embodiment, the invention contemplates a bivalent polypeptide composition defined above in which X is the immunoglobulin light chain constant domain ($C_L$), wherein the light chain constant regions are selected from the group consisting of $C_\kappa$ and $C_\lambda$, having a cysteine residue capable of forming a disulfide bridge, and wherein the composition contains two bivalent polypeptides covalently linked by said disulfide bridge according to the formula:

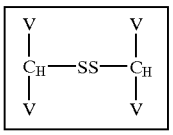

The preparation and use of a bivalent polypeptide is described further herein, and in the Examples.

As used herein with regard to polypeptides, the phrase "operatively linked" means that polypeptide fragments, or protein domains represented by polypeptides, have been covalently joined into a single polypeptide polymer, preferably by conventional amide bonds between the adjacent amino acids being linked in the polypeptide.

In one embodiment, the linkage means is the formation of disulfide bonds between two or more polypeptides comprising constant domains resulting in the covalent linkage of two or more polypeptides. In another embodiment, the linkage means is the formation of an amide bond between adjacent amino acid residues resulting in the formation of a polypeptide comprising one or more constant region domains and two or more variable region domains.

In one embodiment, X is an amino acid residue sequence that defines the constant region of an immunoglobulin constant region polypeptide. In a particularly preferred polypeptide X is a heavy chain ($C_H$) or light chain ($C_L$) polypeptide, wherein $C_L$ is selected from the group consisting of $C_\kappa$ and $C_\lambda$.

The individual $C_H$ and $C_L$ domains can be produced in lengths equal to or substantially equal to their naturally occurring lengths. However, in preferred embodiments, the $C_H$ and $C_L$ polypeptides will generally have fewer than 125 amino acid residues, more usually fewer than about 120 amino acid residues, while normally having greater than 60 amino acid residues, usually greater than about 95 amino acid residues, more usually greater than about 100 amino acid residues. Preferably, the $C_H$ will be from about 110 to about 230 amino acid residues in length while $C_L$ will be from about 95 to about 214 amino acid residues in length. $C_H$ and $C_L$ chains sufficiently long to form bispecific and/or bivalent molecules are preferred.

Those individual $C_H$ and $C_L$ domains which are produced in lengths equal to or substantially equal to their naturally occurring lengths typically contain one or more of the amino acid residue cysteine at or near the 3' end of the polypeptide. The cysteine residues can form a disulphide bond with cysteine residues present in the same molecule resulting in the formation of one or more intramolecular disulphide bonds or between two or more molecules resulting in the formation of one or more intermolecular disulphide bonds.

In a related embodiment, X is an amino acid residue sequence that defines a portion of the constant region of an immunoglobulin constant region polypeptide. In a particularly preferred polypeptide X is a heavy chain ($C_H$) or light chain ($C_L$) polypeptide, wherein $C_L$ is selected from the group consisting of $C_\kappa$ and $C_\lambda$.

The individual $C_H$ and $C_L$ domains can be produced in lengths lesser than their naturally occurring lengths. In preferred embodiments, the $C_H$ and $C_L$ polypeptides will generally have fewer than 40 amino acid residues, more usually fewer than about 30 amino acid residues, while normally having greater than 3 amino acid residues, usually greater than about 5 amino acid residues, more usually greater than about 8 amino acid residues. Preferably, the $C_H$ will be from about 12 to about 20 amino acid residues in length while $C_L$ will be from about 12 to about 25 amino acid residues in length. $C_H$ and $C_L$ chains sufficiently long to form bispecific and/or bivalent molecules are preferred.

Those individual $C_H$ and $C_L$ domains which are produced in lengths less than their naturally occurring lengths typically are used to directly link one or more variable regions, V, by the formation of an amide bond between adjacent amino acid residues resulting in the formation of a single polypeptide comprising one or more constant region domains and two or more variable region domains.

In one embodiment, the $C_H$ is selected from the group consisting of the immunoglobulin classes IgG, IgA, IgM, IgD and IgE. In a preferred embodiment, the $C_H$ is selected from the immunoglobulin class IgG and is selected from the group of IgG1 subclasses consisting of IgG1, IgG2, IgG3, and IgG4. In a preferred embodiment, $C_L$ is selected from the group consisting of $C_\kappa$ and $C_\lambda$.

Typically the constant region domains of the $C_H$ and $C_L$ polypeptides will have a lesser variety of sequences than the variable region domains and hence will represent fewer number of unique sequences. Variations in the amino acid residue sequence are represented by the different classes, subclasses, isotypic variants, and allotypes of heavy and light chain immunoglobulins and are well known to those of skill in the art.

In one embodiment, V is an amino acid residue sequence that defines the ligand or antigen binding domain of an immunoglobulin variable region polypeptide. In a particularly preferred polypeptide V is a $V_H$ or $V_L$ polypeptide.

A polypeptide of the present invention assumes a conformation having a binding site specific for, as evidenced by its ability to be competitively inhibited, a preselected or predetermined ligand such as an antigen, hapten, enzymatic substrate and the like. In one embodiment, a receptor of this invention is a ligand binding polypeptide that forms an antigen binding site which specifically binds to a preselected antigen to form a complex having a sufficiently strong binding between the antigen and the binding site for the complex to be isolated. When the receptor is an antigen binding polypeptide its affinity or avidity is generally greater than $10^5$ $M^{-1}$ more usually greater than $10^6$ and preferably greater than $10^8$ $M^{-1}$.

One or more of the different polypeptide chains is preferably derived from the variable region of the light and heavy chains of an immunoglobulin. Typically, polypeptides comprising the light ($V_L$) and heavy ($V_H$) variable regions are employed together for binding the preselected ligand.

The individual $V_H$ and $V_L$ domains can be produced in lengths equal to or substantially equal to their naturally occurring lengths. However, in preferred embodiments, the $V_H$ and $V_L$ polypeptides will generally have fewer than 125 amino acid residues, more usually fewer than about 120 amino acid residues, while normally having greater than 60 amino acid residues, usually greater than about 95 amino acid residues, more usually greater than about 100 amino acid residues. Preferably, the $V_H$ will be from about 110 to about 230 amino acid residues in length while $V_L$ will be from about 95 to about 214 amino acid residues in length. $V_H$ and $V_L$ chains sufficiently long to form single chain polypeptides or Fabs are preferred.

Typically the variable regions of the $V_H$ and $V_L$ polypeptides will have a greater variety of sequences than the constant regions and, based on the present strategy, the variable regions can be further modified to permit a variation of the normally occurring $V_H$ and $V_L$ chains. A synthetic polynucleotide can be employed to vary one or more amino acid in a variable region to alter the binding affinity or binding specificity of a variable region.

D. Methods for Producing a Monovalent or Bivalent Polypeptide

1. General Rationale

In one embodiment the present invention provides a method for producing novel polypeptides as described further herein. Although the invention describes both monovalent and bivalent polypeptides, their general preparation depends upon the construction of one or more DNA expression vectors in which a gene encoding an antigen binding site (V) is operatively linked in-frame to a gene encoding an immunoglobulin constant domain (C) so as to form a fusion protein comprised of polypeptide domains not normally associated in nature.

In the preparation of a monovalent polypeptide, having an amino acid residue sequence defined herein by the formula V—C, the method involves operatively linking first and second nucleotide sequences that code for V and C amino acid residue sequences, respectively, to a nucleotide expression vector capable of expressing the monovalent polypeptide. The V and C region genes are linked in frame so as to preserve the frame of the expressed polypeptide, as is well known.

The antibody binding site domain (V) is comprised of heavy and light chain variable domain amino acid residue sequences, and therefore, nucleotide sequences coding the V region can be ordered on the V region gene in either the $V_H$—$V_L$ or $V_L$—$V_H$ orientation as described further herein.

The immunoglobulin constant domain (C) can be a $C_H$ or $C_L$ domain, and therefore, nucleotide sequences encoding the C region can be comprised of either $C_H$ or $C_L$ genes. The nucleotide sequences encoding the $C_L$ region can be comprised of either $C_\kappa$ or $C_\lambda$ genes. The C region gene is operatively linked to the V region genes so as to be in the same reading frame with the encoded V and C domain amino acid residue sequences.

In the preparation of a bivalent polypeptide, having an amino acid residue sequence defined herein by the formula V—X—V, the method involves operatively linking first, second and third nucleotide sequences that code for a first V domain, an X domain and a second V domain amino acid residue sequences, respectively, to a nucleotide expression vector capable of expressing the bivalent polypeptide. The three domain genes (V, X and V) are linked in the same reading frame so as to preserve the frame of the expressed polypeptide.

In one embodiment, the DNA expression vector can be used to express one or more different polypeptides of this invention, and by virtue of the presence of the cysteine residues in the constant domain, the expressed polypeptides can associate to form dimeric and multimeric proteins, thereby forming polypeptide compositions with multiple polypeptide subunits and potentially multiple antigen binding specificities.

In preferred embodiments using a monovalent polypeptide, the disclosure provides for the combined expression of two or more monovalent polypeptides, each having a different antigen-binding site specificity, so as to form upon disulfide bridging a dimeric or multimeric protein composition having multiple ligand binding specificities.

A particular aspect of this embodiment is the production of dimeric polypeptide compositions in which one monovalent polypeptide contains a heavy chain constant domain, and the other monovalent polypeptide contains a light chain constant domain, thereby utilizing the natural disulfide bridging mechanism between heavy and light chains normally found in immunoglobulins to approximate a heavy chain-light chain heterodimer. To that end, the method contemplates the preparation of a first monovalent polypeptide in which a first antibody binding site is fused to CH1 and expressed in a heavy chain cloning cassette, and a second monovalent polypeptide in which a second antibody binding site is fused to a kappa constant domain ($C_\kappa$) in a light chain cloning cassette. Two independent libraries of the first and second directed molecules are thereby constructed and recombined randomly to generate combinatorial bispecific antigen-binding polypeptide molecules. Fusion of the CH1 and kappa constant domain results in predominantly heterodimer formation which could be readily purified on a protein G column by FPLC.

In another particular aspect, the first antibody binding site is fused to a heavy chain constant domain (CH) and expressed in a heavy chain cloning cassette, and the second antibody binding site is fused to a lambda constant domain ($C_\lambda$) in a light chain cloning cassette. Two independent libraries of the first and second molecules are thereby constructed and recombined randomly to generate combinatorial bispecific antigen-binding polypeptide molecules. Fusion of the CH and $C_\lambda$ results in predominantly heterodimer formation which can be readily purified on a protein G column by FPLC.

In another particular aspect of this embodiment is the production of dimeric polypeptide compositions in which both monovalent polypeptides contain a light chain constant domain wherein the light chain constant domain is $C_\kappa$, thereby utilizing the disulfide bridging mechanism between the light chains to approximate a light chain-light chain heterodimer. To that end, the method contemplates the preparation of first and second monovalent polypeptides in which the first and second antibody binding sites are fused to a kappa constant domain ($C_\kappa$) and expressed in the first and second light chain cloning cassettes. Two independent libraries of the first and second molecules are thereby constructed and recombined randomly to generate combinatorial bispecific antigen-binding polypeptide molecules. Fusion of the two kappa constant domains results in predominantly heterodimer formation which could be readily purified on a column which binds the kappa light chain.

In an alternate aspect of this embodiment is the production of dimeric polypeptide compositions in which both monovalent polypeptides contain a light chain constant domain wherein the light chain constant domains are selected from the group consisting of $C_\kappa$ and $C_\lambda$, thereby utilizing the disulfide bridging mechanism between the light chains to approximate a light chain-light chain heterodimer. To that end, the method contemplates the preparation of a first monovalent polypeptide in which a first antibody binding site is fused to a kappa constant domain ($C_\kappa$) and expressed in a light chain cloning cassette, and a second monovalent polypeptide in which a second antibody binding site is fused to a lambda constant domain ($C_\lambda$) in a light chain cloning cassette. Two independent libraries of the first and second directed molecules are thereby constructed and recombined randomly to generate combinatorial bispecific antigen-binding polypeptide molecules. Fusion of the kappa and lambda constant domains results in predominantly heterodimer formation which could be readily purified by sequential purification with a first column which binds the kappa light chain and a second column which binds the lambda light chain resulting in a relatively homogenous product containing the kappa and lambda constant domains. Also contemplated is a first column which binds the lambda light chain and a second column which binds the kappa light chain resulting in a relatively homogenous product containing the kappa and lambda constant domains.

In an additional aspect of this embodiment is the production of dimeric polypeptide compositions in which both monovalent polypeptides contain a light chain constant domain wherein the light chain constant domain is $C_\lambda$, thereby utilizing the disulfide bridging mechanism between the light chains to approximate a light chain-light chain heterodimer. To that end, the method contemplates the preparation of first and second monovalent polypeptides in which the first and second antibody binding sites are fused to separate lambda constant domains ($C_\lambda$) and expressed in first and second light chain cloning cassettes. Two independent libraries of the first and second molecules are thereby constructed and recombined randomly to generate combinatorial bispecific antigen-binding polypeptide molecules. Fusion of the lambda constant domains results in predominantly heterodimer formation which could be readily purified by a column which binds the lambda light chain.

In another embodiment, a bispecific tetravalent polypeptide molecule can be prepared. Following the construction of cloning vectors for expressing whole antibodies in mammalian cells with readily compatible cloning sites, one transfers the antibody binding site domain (V in the form of $V_H$—$V_L$) directly to the appropriate cloning cassette generating first an entire heavy chain and second a light chain-like polypeptide combination. upon expression, the molecule produced from such a construction assembles into a first H—L like heterodimer and then self associates to form a molecule that is tetravalent (four binding sites) yet bispecific for the desired specificities. This could be a very potent molecule in a therapeutic setting since this would permit the utilization of the natural effector of the antibody Fc region.

Extending the possible combinations further, one can prepare trispecific or trivalent or hexavalent polypeptide molecules. To that end, a bivalent polypeptide vector is first prepared having a heavy chain constant domain. A monovalent polypeptide vector is also prepared having a light chain constant domain, and the two polypeptides are co-expressed in the same expression medium. The light chain constant domains are selected from the group consisting of kappa ($C_\kappa$) and lambda ($C_\lambda$) light chain constant domains. The expressed polypeptides assemble first to form a monovalent-bivalent polypeptide pair, thereby forming a trivalent polypeptide composition, and the formed polypeptide self-associates to produce a hexavalent polypeptide.

In a related embodiment, one can construct a tetraspecific and tetravalent polypeptide composition by using two bivalent polypeptides in which each antibody binding site is directed to a different ligand. The two bivalent polypeptide chains are co-expressed in a single expression medium, allowing their assembly to form a dimeric polypeptide composition that is tetravalent and tetraspecific.

2. Production of Immunoglobulin Variable and Constant Domain Genes

Methods for preparing fragments of genomic DNA from which immunoglobulin variable and constant region genes can be cloned are well known in the art. See for example Herrmann et al., *Methods In Enzymol.*, 152:180–183, (1987); Frischauf, *Methods In Enzymol.*, 152:183–190 (1987); Frischauf, *Methods In Enzymol.*, 152:190–199 (1987); and DiLella et al., *Methods In Enzymol.*, 152:199–212 (1987). (The teachings of the references cited herein are hereby incorporated by reference.)

The desired immunoglobulin genes can be isolated from either genomic material containing the gene expressing the variable region or the messenger RNA (mRNA) which represents a transcript of the variable region. The difficulty in using the genomic DNA from other than non-rearranged B lymphocytes is in juxtaposing the sequences coding for the variable region, where the sequences are separated by introns. The DNA fragment(s) containing the proper exons must be isolated, the introns excised, and the exons then spliced in the proper order and in the proper orientation. For the most part, this will be difficult, so that the alternative technique employing rearranged B cells will be the method of choice because the V, D and J immunoglobulin gene regions have translocated to become adjacent, so that the sequence is continuous (free of introns) for the entire variable regions.

Where mRNA is utilized the cells will be lysed under RNase inhibiting conditions. In one embodiment, the first step is to isolate the total cellular mRNA. Poly A+ mRNA can then be selected by hybridization to an oligo-dT cellulose column. Selected polyA+ mRNA is then converted to double-stranded DNA and inserted into an appropriate vector by methods well known to those of skill in the art to produce a cDNA library. The cDNA library contains DNA inserts representing mRNAs expressed in the cells, including those which code for the expression of heavy and light chain polypeptides, from which the mRNA was derived.

The presence of DNA inserts coding for the heavy and/or light chain polypeptides present in the cDNA library can be identified by hybridization with single-stranded DNA of the appropriate genes. Conveniently, the sequences coding for the constant portion of the heavy and/or light chain polypeptides can be used as polynucleotide probes, which sequences can be obtained from available sources. See for example, Early and Hood, *Genetic Engineering,* Setlow and Hollaender, eds., Vol. 3, Plenum Publishing Corporation, NY, (1981), pages 157–188; and Kabat et al., *Sequences of Immunological Interest,* National Institutes of Health, Bethesda, Md., (1987).

In preferred embodiments, the preparation containing the total cellular mRNA is first enriched for the presence of $C_H$, $C_L$, $V_H$ and/or $V_L$ coding mRNA. A preferred source of mRNA is a hybridoma capable of secreting monoclonal antibodies directed to a specific antigen. An additional preferred source of mRNA are cells which express antibodies directed to a plurality of antigens isolated from mouse, rat, rabbit and human. A particularly preferred source of cells which express antibody are isolated from human. Enrichment is typically accomplished by subjecting the total mRNA preparation or partially purified mRNA product thereof to a primer extension reaction employing a polynucleotide synthesis primer as described herein. Exemplary methods for producing $V_H$ and $V_L$ gene repertoires using polynucleotide synthesis primers are described in PCT Application No. PCT/US 90/02836 (International Publication No. WO 90/14430). Particularly preferred methods for producing a gene repertoire rely on the use of preselected oligonucleotides as primers in a polymerase chain reaction (PCR) to form PCR reaction products as described herein.

In preferred embodiments, isolated B cells are immunized in vitro against a preselected antigen. In vitro immunization is defined as the clonal expansion of epitope-specific B cells in culture, in response to antigen stimulation. The end result is to increase the frequency of antigen-specific B cells in the immunoglobulin repertoire, and thereby decrease the number of clones in an expression library that must be screened to identify a clone expressing an antibody of the desired specificity. The advantage of in vitro immunization is that human monoclonal antibodies can be generated against a limitless number of therapeutically valuable antigens, including toxic or weak immunogens. For example, antibodies specific for the polymorphic determinants of tumor-associated antigens, rheumatoid factors, and histocompatibility antigens can be produced, which can not be elicited in immunized animals. In addition, it may be possible to generate immune responses which are normally suppressed in vivo. Exemplary immune responses which are normally suppressed in vivo are those responses to human cell surface markers.

In vitro immunization can be used to give rise to either a primary or secondary immune response. A primary immune response, resulting from first time exposure of a B cell to an antigen, results in clonal expansion of epitope-specific cells and the secretion of IgM antibodies with low to moderate apparent affinity constants ($10^6$–$10^8$ M$^{-1}$). Primary immunization of human splenic and tonsillar lymphocytes in culture can be used to produce monoclonal antibodies against a variety of antigens, including cells, peptides, macromolecule, haptens, and tumor-associated antigens. Memory B cells from immunized donors can also be stimulated in culture to give rise to a secondary immune response characterized by clonal expansion and the production of high affinity antibodies (>$10^9$ M$^{-1}$) of the IgG isotype, particularly against viral antigens by clonally expanding sensitized lymphocytes derived from seropositive individuals.

In one embodiment, peripheral blood lymphocytes are depleted of various cytolytic cells that appear to downmodulate antigen-specific B cell activation. When lysosome-rich subpopulations (natural killer cells, cytotoxic and suppressor T cells, monocytes) are first removed by treatment with the lysosmotropic methyl ester of leucine, the remaining cells (including B cells, T helper cells, accessory cells) respond antigen-specifically during in vitro immunization. The lymphokine requirements for inducing antibody production in culture are satisfied by a culture supernatant from activated, irradiated T cells.

In addition to in vitro immunization, cell panning (immunoaffinity absorption) can be used to further increase the frequency of antigen-specific B cells. Techniques for selecting B cell subpopulations via solid-phase antigen binding are well established. Panning conditions can be optimized to selectively enrich for B cells which bind with high affinity to a variety of antigens, including cell surface proteins. Panning can be used alone, or in combination with in vitro immunization to increase the frequency of antigen-specific cells above the levels which can be obtained with either technique alone. Immunoglobulin expression libraries constructed from enriched populations of B cells are biased in favor of antigen-specific antibody clones, and thus, enabling identification of clones with the desired specificities from smaller, less complex libraries.

3. Preparation of Polynucleotide Primers

The term "polynucleotide" as used herein in reference to primers, probes and nucleic acid fragments or segments to be synthesized by primer extension is defined as a molecule comprised of two or more deoxyribonucleotide or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH.

The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057–70 (1984); Studier et al., *J. Mol. Biol.*, 189:113–130 (1986); and *Molecular Cloning: A Laboratory Manual. Second Edition,* Maniatis et al., eds., Cold Spring Harbor, N.Y. (1989).

When a primer containing a DNA-dependent RNA polymerase promoter is used the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology,* 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.,* 89:719–736 (1974).

The polynucleotide primers can be prepared using any suitable method, such as, for example, the phosphotriester or phosphodiester methods see Narang et al., *Meth. Enzymol.,* 68:90, (1979); U.S. Pat. No. 4,356,270; and Brown et al., *Meth. Enzymol.,* 68:109, (1979).

The choice of a primer's nucleotide sequence depends on factors such as the distance on the nucleic acid from the region coding for the desired receptor, its hybridization site on the nucleic acid relative to any second primer to be used, the number of genes in the repertoire it is to hybridize to, and the like. Additional nucleotide sequences may also be added to the 5' non-priming portion of the primer. Such nucleotide sequences may represent restriction enzyme recognition sites, translational stop codons and the like.

4. Polymerase Chain Reaction to Produce Cloned Variable and Constant Immunoglobulin Genes The strategy used for cloning the $C_H$, $C_L$, $V_H$ and/or $V_L$ genes contained within a repertoire will depend, as is well known in the art, on the type, complexity, and purity of the nucleic acids making up the repertoire. Other factors include whether or not the genes are contained in one or a plurality of repertoires and whether or not they are to be amplified and/or mutagenized.

The immunoglobulin gene repertoires are comprised of polynucleotide coding strands, such as mRNA and/or the sense strand of genomic DNA. If the repertoire is in the form of double stranded genomic DNA, it is usually first denatured, typically by melting, into single strands. A repertoire is subjected to a PCR reaction by treating (contacting) the repertoire with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the repertoire. The first primer of a PCR primer pair is sometimes referred to herein as the "sense primer" because it hybridizes to the coding or sense strand of a nucleic acid. In addition, the second primer of a PCR primer pair is sometimes referred to herein as the "anti-sense primer" because it hybridizes to a non-coding or anti-sense strand of a nucleic acid, i.e., a strand complementary to a coding strand.

The PCR reaction is performed by mixing the PCR primer pair, preferably a predetermined amount thereof, with the nucleic acids of the repertoire, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different $V_H$-coding and/or $V_L$-coding DNA homologs.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined to increase the diversity of the gene library.

In another strategy, the object is to clone the immunoglobulin genes from a repertoire by providing a polynucleotide complement of the repertoire, such as the anti-sense strand of genomic dsDNA or the polynucleotide produced by subjecting mRNA to a reverse transcriptase reaction. Methods for producing such complements are well known in the art.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10_6$:1 primer:template) of the primer is admixed to the buffer containing the template strand. A large molar excess is preferred to improve the efficiency of the process.

The PCR buffer also contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 uM dATP; 200 uM dTTP; 200 uM dCTP; 200 uM dGTP; and 2.5 units *Thermus aquaticus* DNA polymerase I (U.S. Pat. No. 4,889,818) per 100 microliters of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acid Res.*, 17:711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

The first and/or second PCR reactions discussed above can advantageously be used to incorporate into the receptor a preselected epitope useful in immunologically detecting and/or isolating a receptor. This is accomplished by utilizing a first and/or second polynucleotide synthesis primer or expression vector to incorporate a predetermined amino acid residue sequence into the amino acid residue sequence of the receptor.

After producing immunoglobulin gene DNA homologs for a plurality of different immunoglobulin genes within the repertoires, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector. PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,195, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

In preferred embodiments only one pair of first and second primers is used per amplification reaction. The amplification reaction products obtained from a plurality of different amplifications, each using a plurality of different primer pairs, are then combined.

However, the present invention also contemplates DNA homolog production via co-amplification (using two pairs of primers), and multiplex amplification (using up to about 8, 9 or 10 primer pairs).

In preferred embodiments, the PCR process is used not only to produce a library of DNA molecules, but also to induce mutations within the library or to create diversity from a single parental clone and thereby provide a library having a greater heterogeneity. First, it should be noted that the PCR process itself is inherently mutagenic due to a variety of factors well known in the art. Second, in addition to the mutation inducing variations described in the above referenced U.S. Pat. No. 4,683,195, other mutation inducing PCR variations can be employed. For example, the PCR reaction admixture, can be formed with different amounts of one or more of the nucleotides to be incorporated into the extension product. Under such conditions, the PCR reaction proceeds to produce nucleotide substitutions within the extension product as a result of the scarcity of a particular base. Similarly, approximately equal molar amounts of the nucleotides can be incorporated into the initial PCR reaction admixture in an amount to efficiently perform X number of cycles, and then cycling the admixture through a number of cycles in excess of X, such as, for instance, 2X. Alternatively, mutations can be induced during the PCR reaction by incorporating into the reaction admixture nucleotide derivatives such as inosine, not normally found in the nucleic acids of the repertoire being amplified. During subsequent in vivo DNA synthesis and replication of the nucleic acids in a host cell, the nucleotide derivative will be replaced with a substitute nucleotide thereby inducing a point mutation.

5. Ligation Reactions to Produce Vectors

In preparing a vector of this invention, a ligation admixture is prepared as described above, and the admixture is subjected to ligation conditions for a time period sufficient for the admixed polypeptide genes to ligate (become operatively linked) to the plurality of DNA expression vectors to form the library.

Ligation conditions are conditions selected to favor a ligation reaction wherein a phosphodiester bond is formed between adjacent 3' hydroxyl and 5' phosporyl termini of DNA. The ligation reaction is preferably catalyzed by the enzyme T4 DNA ligase. Ligation conditions can vary in time, temperature, concentration of buffers, quantities of DNA molecules to be ligated, and amounts of ligase, as is well known. Preferred ligation conditions involve maintaining the ligation admixture at 4 degrees Centigrade (4° C.) to 12° C. for 1 to 24 hours in the presence of 1 to 10 units of T4 DNA ligase per milliliter (ml) and about 1 to 2 micrograms (ug) of DNA. Ligation buffer in a ligation admixture typically contains 0.5 M Tris-HCl (pH 7.4), 0.01 M $MgCl_2$, 0.01 M dithiothreitol, 1 mM spermidine, 1 mM ATP and 0.1 mg/ml bovine serum albumin (BSA). Other ligation buffers can also be used.

Exemplary ligation reactions are described in Example 3.

6. Purification of Polypeptides

Conventional methods of purifying polypeptides comprising antibodies include precipitation and column chromatography and are well known to one of skill in the purification arts. The method of purification used is dependent upon several factors including the purity required, the source of the antibody, the intended use for the antibody, the species in which the antibody was produced, the class of the antibody and, when the antibody is a monoclonal antibody, the subclass of the antibody.

A commonly used method of purification is affinity chromatography in which the antibody to be purified is bound by protein A, protein G or by an anti-immunoglobulin antibody. Another method of affinity chromatography, which is well known to those of skill in the art, is the specific binding of the antibody to its respective antigen.

a) Purifiction with Protein A or G

In one embodiment, an antibody is purified in a single purification step by specific binding of the antibody to protein A or G using well known methods. Non-specifically bound molecules are removed in a wash step and the specifically bound antibody is eluted.

b) Purification with Antigen

In another embodiment, an antigen is effective in the isolation of polypeptides comprising a variable region domain which specifically binds the antigen.

In an alternative embodiment, the antibody comprising a variable region domain is specifically bound to a single antigen. In a sequential purification procedure, the bispecific antibody comprising two or more variable domains is specifically bound to a first antigen and then to a second antigen. In a preferred embodiment, the first and second antigen are selected from the group consisting of progesterone, NPN, DPN, CD3 and CD4.

In an alternative embodiment, a bispecific antibody comprising two or more variable regions is purified by sequential purification by specifically binding the antibody to a first antigen in a first purification step and to a second antigen in a second purification step.

c) Purification with Anti-IgG Antibodies

Variations in the amino acid residue sequence of the constant region domains of antibodies result in constant region domains which are immunologically distinct. Thus, antibodies can be produced which specifically bind specific classes, subclasses, isotypic variants, and even allotypes of the heavy and light chain constant regions. Such antibodies which specifically bind to the immunologically distinct constant region domains can be used to distinguish between and to purify polypeptides comprising the constant region domains.

In one embodiment, an anti-immunoglobulin antibody is effective in the isolation of polypeptides comprising a constant region domain which is immunologically distinct from other constant region domains.

The method of purifying an antibody with an anti-immunoglobulin antibody can be either a single purification procedure or a sequential purification procedure. Methods of single and sequential purification are well known to those in the purification arts. In a single-step purification procedure, the antibody is specifically bound by a single anti-immunoglobulin antibody. Non-specifically bound molecules are removed in a wash step and the specifically bound molecules are specifically eluted. In a sequential purification procedure, the antibody is specifically bound to a first anti-immunoglobulin antibody, non-specifically bound molecules are removed in a wash step, and the specifically bound molecules are specifically eluted. The eluant from the first anti-immunoglobulin antibody is then specifically bound to a second anti-immunoglobulin antibody. The non-specifically bound molecules are removed in a wash step, and the specifically bound molecules are specifically eluted. In a preferred embodiment, the antibody is sequentially purified by a first and second anti-immunoglobulin antibody selected from the group consisting of antibodies which specifically bind heavy and light chain constant regions. In a more preferred embodiment, the antibody is sequentially purified by a first and second anti-immunoglobulin antibody selected from the group consisting of antibodies which specifically bind the heavy chain constant region of IgG and light chain constant regions of kappa and lambda. In an even more preferred embodiment, the anti-immunoglobulin antibody is selected from the group consisting of antibodies which specifically bind the light chain constant regions of kappa and lambda.

In a preferred embodiment, an antibody of this invention comprising the kappa and lambda constant region domains is sequentially purified by affinity chromatography. In this method, first and second affinity columns are prepared comprising anti-kappa and anti-lambda antibodies. The anti-kappa and anti-lambda antibodies used correspond to the genus of polypeptide to be purified, e.g., if a human kappa constant region is to be purified, an anti-human kappa light chain antibody is used. First, 16 mgs of goat anti-human kappa light chain antibody is admixed with 8 ml Gamma-bind beads (Pharmacia, Piscataway, N.J.). The beads and antibody are mixed on a rocker at room temperature for 1 hour. The beads are washed twice with 10 volumes of 0.2 M sodium borate, pH 9.0, to remove unbound antibody. The washed beads are resuspended in 10 volumes of 0.2 M sodium borate, pH 9.0. The concentration of (dimethylaminomethyl)phenol (DMP) is brought to 20 mM. Ten microliters of the beads are removed to determine coupling efficiency by gel electrophoresis. The beads are admixed with the DMP on a rocker at room temperature for 30 minutes. Ten microliters of the beads are removed to determine coupling efficiency by gel electrophoresis. The coupling reaction is stopped by washing the beads once in 0.2 M ethanolamine, pH 8.0, and subsequently incubating at room temperature in 0.2 M ethanolamine, pH 8.0, on a rocker. The beads are allowed to settle or are centrifuged and the beads resuspended in PBS and thimerosol (0.05% w/v) added prior to storage. Prior to the purification of antibodies of this invention, the column is washed with 3 column volumes of 10.8% buffer B (buffer B is 0.1 M sodium phosphate (dibasic) and 0.5 M NaCl) and 98.2% buffer A (buffer A is 0.05 M citric acid (free acid) and 0.5 M NaCl) to remove non-DMP bound antibodies. The efficiency of the coupling reaction is determined by comparison of the two aliquots of beads which were removed before and after the coupling reaction by SDS PAGE gel electrophoresis. Beads with coupled antibody are used to prepare a column.

The pH of a solution containing antibodies to be purified is adjusted to 7.4. Supernatants containing antibodies are filtered through a 0.22 micron filter. Flow rates for loading samples containing antibody are generally 1 to 2 ml per minute. Washing and elution flow rates are usually. 3 to 4 ml per minute. The column is equilibrated with at least 3 column volumes of 87.2% buffer B.

Typically, 20 ml of sample containing the antibody to be purified is loaded onto a 10 ml column of beads with coupled anti-kappa light chain antibody. The sample is then washed with 100 ml of 87.2% buffer B and 12.8% buffer A. The bound antibody is then eluted with 10.8% buffer B and 98.2% buffer A which is pH 2.3. The eluted antibody is neutralized with 1 M tris, pH 9.0. Eluted fractions containing antibody are concentrated until the desired antibody concentration is reached. The antigen binding activity of the purified antibody can be determined in an ELISA assay as described in the Examples and the purity of the antibody assessed by SDS PAGE gel analysis.

Affinity matrices comprising anti-immunoglobulin antibodies can be prepared using the methods described above with anti-lambda and anti-heavy chain constant domains antibodies to purify antibodies comprising lambda and heavy chain constant domains, respectively.

In an alternative embodiment, a bispecific antibody is purified by sequential purification by specifically binding the antibody to a first antigen in a first purification step and to a second antigen in a second purification step by methods well known to those in the purification arts.

Also contemplated is sequential purification by specifically binding the antibody to a first antigen in a first purification step and to an anti-immunoglobulin antibody in a second purification step. In an alternative embodiment, the antibody is purified by sequential purification by specifically binding the antibody to a first anti-immunoglobulin antibody in a first purification step and then to a second antigen in a second purification step.

Also contemplated is sequential purification by specifically binding the antibody to a first antigen in a first purification step and to an anti-immunoglobulin antibody in a second purification step. In an alternative embodiment, the antibody is purified by sequential purification by specifically binding the antibody to a first anti-immunoglobulin antibody in a first purification step and then to a second antigen in a second purification step.

In a preferred method, sequential purification with a first and second antibody is effective in the isolation of two or more polypeptides joined by disulfide bonding comprising constant region domains which are specifically bound by a first and second antibody.

E. Diagnostic Methods

The present invention also describes a diagnostic system, preferably in kit form, for assaying for the presence of a preselected ligand, or antigen, in a sample where it is desirable to detect the presence, and preferably the amount, of the ligand,or antigen in a sample according to the diagnostic methods described herein.

In one embodiment, the antigen is progesterone or the cell surface molecules CD4 and CD3.

The sample can be a tissue, tissue extract, fluid sample or body fluid sample, such as blood, plasma or serum.

The diagnostic system includes, in an amount sufficient to perform at least one assay, a polypeptide composition according to the present invention, as a separately packaged reagent.

Exemplary diagnostic systems for detecting a preselected ligand in the solid phase and utilizing a polypeptide composition of this invention are described in the Examples.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a polypeptide of the present invention. Thus, for example, a package can be a glass vial used to contain milligram quantities of a contemplated labeled polypeptide preparation, or it can be a microtiter plate well to which microgram quantities of a contemplated polypeptide has been operatively affixed, i.e., linked so as to be capable of binding a ligand.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

A diagnostic system of the present invention preferably also includes a label or indicating means capable of signaling the formation of a binding reaction complex containing a ligand-binding polypeptide complexed with the preselected ligand.

The word "complex" as used herein refers to the product of a specific binding reaction such as a polypeptide-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed polypeptide, or phage particle that is used in a diagnostic method. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool,* Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$ indium of $^{3}H$.

The linking of labels, i.e., labeling of, polypeptides and proteins or phage is well known in the art. For instance, proteins can be labeled by metabolic incorporation of radioisotope-containing amino acids provided as a component in the culture medium. See, for example, Galfre et al., Meth. Enzymol., 73:3–46 (1981). The techniques of protein conjugation or coupling through activated functional groups are particularly applicable. See, for example, Aurameas, et al., Scand. J. Immunol., Vol. 8 Suppl. 7:7–23 (1978), Rodwell et al., Biotech., 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide of the present invention. Exemplary specific binding agents are antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of a preselected ligand in a fluid sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample and is readily applicable to the present methods. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in some embodiments, a polypeptide of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

F. Assay Methods

The present invention contemplates various assay methods for determining the presence, and preferably amount, of a preselected ligand, typically present in an aqueous composition such as a biological fluid sample using a polypeptide composition of this invention as an ligand-binding reagent to form a binding reaction product whose amount relates, either directly or indirectly, to the amount of the preselected ligand in the sample.

Those skilled in the art will understand that there are numerous well known clinical diagnostic chemistry procedures in which a binding reagent of this invention can be used to form an binding reaction product whose amount relates to the amount of the ligand in a sample. Thus, while exemplary assay methods are described herein, the invention is not so limited.

Various heterogenous and homogeneous protocols, either competitive or noncompetitive, can be employed in performing an assay method of this invention.

In one embodiment, the invention contemplates a direct binding assay using a polypeptide composition of this invention as a binding reagent to detect the presence of a preselected ligand with which the polypeptide binds. The method comprises the steps of a) admixing a sample suspected to contain a preselected antigen with a polypeptide of this invention that binds to the preselected ligand under binding conditions sufficient for the polypeptide to bind the ligand and form a ligand-receptor complex; and b) detecting the presence of the ligand-receptor complex or the polypeptide in the complex.

Binding conditions are those that maintain the ligand-binding activity of the receptor. Those conditions include a temperature range of about 4 to 50 degrees Centigrade, a pH value range of about 5 to 9 and an ionic strength varying from about that of distilled water to that of about one molar sodium chloride.

The detecting step can be directed, as is well known in the immunological arts, to either the complex or the binding reagent (the receptor component of the complex). Thus, a secondary binding reagent such as an antibody specific for the receptor may be utilized.

Alternatively, the complex may be detectable by virtue of having used a labeled receptor molecule, thereby making the complex labeled. Detection in this case comprises detecting the label present in the complex.

A further diagnostic method utilizes the multivalency of a polypeptide composition of this invention to cross-link ligand, thereby forming an aggregation of multiple ligands and polypeptides, producing a precipitable aggregate. This embodiment is comparable to the well known methods of immune precipitation. This embodiment comprises the steps of admixing a sample with a polypeptide composition of this invention to form a binding admixture under binding conditions, followed by a separation step to isolate the formed binding complexes. Typically, isolation is accomplished by centrifugation or filtration to remove the aggregate from the admixture. The presence of binding complexes indicates the presence of the preselected ligand to be detected.

G. Therapeutic Methods

The antibodies can also be used immunotherapeutically. The term "immunotherapeutically" or "immunotherapy" as used herein in conjunction with the antibodies of the invention denotes both prophylactic as well as therapeutic administration. Thus, the antibodies can be administered to high-risk patients in order to lessen the likelihood and/or severity of disease, administered to patients already evidencing active infection, or administered to patients at risk of infection.

1. Therapeutic Compositions

The present invention therefore contemplates therapeutic compositions useful for practicing the therapeutic methods described herein. Therapeutic compositions of the present invention contain a physiologically tolerable carrier together with at least one species of antibody as described herein, dissolved or dispersed therein as an active ingredient. In a preferred embodiment, the therapeutic composition is not immunogenic when administered to a human patient for therapeutic purposes, unless that purpose is to induce an immune response.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains an antibody of the present invention, typically an amount of at least 0.1 weight percent of antibody per weight of total therapeutic composition. A weight percent is a ratio by weight of antibody to total composition. Thus, for example, 0.1 weight percent is 0.1 grams of antibody per 100 grams of total composition.

2. Therapeutic Methods

In view of demonstrating T cell crosslinking and activation with bivalent antibodies of the present invention, the present disclosure provides for a method for activating and crosslinking T cells in vitro or in vivo. The method comprises contacting a sample believed to contain effector and helper T cells with a composition comprising a therapeutically effective amount of an antibody of this invention.

For in vivo modalities, the method comprises administering to the patient a therapeutically effective amount of a physiologically tolerable composition containing an antibody of the invention. Thus, the present invention describes in one embodiment a method for activating T cells in a human comprising administering to the human an immunotherapeutically effective amount of the antibody of this invention.

A representative patient for practicing the present immunotherapeutic methods is any human exhibiting symptoms of a disease which may be treated by the activation of T cells or any patient at risk for a disease which may be treated by the activation of T cells.

A therapeutically (immunotherapeutically) effective amount of an antibody is a predetermined amount calculated to achieve the desired effect, i.e., to specifically bind T cells present in the sample or in the patient, and thereby activate the T cells in the sample or patient. In the case of in vivo therapies, an effective amount can be measured by improvements in one or more symptoms associated with disease occurring in the patient, or by serological increases in the numbers of activated T cells.

Thus, the dosage ranges for the administration of the antibodies of the invention are those large enough to produce the desired effect in which the symptoms of the disease are ameliorated or the likelihood of infection decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The antibodies of the invention can be administered parenterally by injection or by gradual infusion over time. Although the infection may be systemic and therefore most often treated by intravenous administration of therapeutic compositions, other tissues and delivery means are contemplated where there is a likelihood that targeting a tissue will result in a lessening of the disease. Thus, antibodies of the invention can be administered intravenously, intraperitoneally, intramuscularly, subcutaneously, intracavity, transdermally, and can be delivered by peristaltic means.

The therapeutic compositions containing an antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of an antibody, a diagnostic method for detecting the antibody in the subject's blood is useful to characterize the fate of the administered therapeutic composition.

The invention also relates to a method for preparing a medicament or pharmaceutical composition comprising an antibody of the invention, the medicament being used for immunotherapy of a related disease.

EXAMPLES

The following examples are intended to illustrate, but not limit, the scope of the invention.

1. Preparation of Mouse cDNA Library from an Anti-Progesterone Hybridoma

A. Preparation of cDNA Containing Variable Heavy and Light Chain DNA Sequences

Total cellular RNA was prepared from $1 \times 10^8$ DB3 hybridoma cells that secrete mouse anti-progesterone antibodies. The DB3 cells were produced following immunization with progesterone using standard hybridoma technology, and can be readily reproduced. The selection of DB3 cells is not considered to be limiting but merely illustrative of the present invention.

The DB3 hybridoma cells were pelleted and then washed with PBS and resuspended in 9 milliliters (ml) of phosphate-buffered saline (PBS). Total RNA was isolated from the cells using the RNA preparation methods described by Chomczynski et al., *Anal Biochem.*, 162:156–159 (1987) and using the RNA isolation kit (Stratagene) according to the manufacturer's instructions. Briefly, the cells were homogenized in 10 ml of a denaturing solution containing 4.0 M guanine isothiocyanate, 0.25 M sodium citrate at pH 7.0, and 0.1 M beta-mercaptoethanol using a glass homogenizer. One ml of sodium acetate at a concentration of 2 M at pH 4.0 was admixed with the homogenized cells. Ten ml of phenol that had been previously saturated with $H_2O$ was also admixed to the denaturing solution. Two ml of a chloroform:isoamyl alcohol (24:1 v/v) mixture was added to this homogenate. The homogenate was mixed vigorously for ten seconds and maintained on ice for 15 minutes. The homogenate was then transferred to a thick-walled 50 ml polypropylene centrifuged tube (Fisher Scientific Company, Pittsburg, Pa.). The solution was centrifuged at 10,000×g for 20 minutes at 4 degrees Celsius (4° C.). The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three ml of isopropyl alcohol was added to the re-suspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then re-suspended in dimethyl pyrocarbonate (DEPC) treated (DEPC-$H_2O$) $H_2O$.

Messenger RNA (mRNA) enriched for sequences containing long poly A tracts was prepared from the total cellular RNA using methods described in *Molecular Cloning: A Laboratory Manual*, Maniatis et al., eds., Cold Spring Harbor, N.Y., (1982). Briefly, one half of the total RNA isolated from the hybridoma cells prepared as described above was re-suspended in 1 ml of DEPC-$H_2O$ and maintained at 65° C. for five minutes. One ml of 2× high salt loading buffer consisting of 100 mM Tris-HCl (Tris [hydroxymethyl] amino methane hydrochloride), 1 M sodium chloride (NaCl), 2.0 mM disodium ethylene diamine tetra-acetic acid (EDTA) at pH 7.5, and 0.2% sodium dodecyl sulfate (SDS) was added to the re-suspended RNA and the mixture allowed to cool to room temperature. The mixture was then applied to an oligo-dT (Collaborative Research Type 2 or Type 3) column that was previously prepared by washing the oligo-dT with a solution containing 0.1 M sodium hydroxide and 5 mM EDTA and then equilibrating the column with DEPC-$H_2O$. The eluate was collected in a sterile polypropylene tube and reapplied to the same column after heating the eluate for 5 minutes at 65° C. The oligo dT column was then washed with 2 ml of high salt loading buffer consisting of 50 mM Tris-HCl at pH 7.5, 500 mM NaCl, 1 mM EDTA at pH 7.5 and 0.1% SDS. The oligo dT column was then washed with 2 ml of 1× medium salt buffer consisting of 50 mM Tris-HCl at pH 7.5, 100 mM, 1 mM EDTA and 0.1% SDS. The messenger RNA was eluted from the oligo dT column with 1 ml of buffer consisting of 10 mM Tris-HCl, pH 7.5, 1 mM EDTA, at pH 7.5, and 0.05% SDS. The messenger RNA was purified by extracting this solution with phenol/chloroform followed by a single extraction with 100% chloroform. The messenger RNA was concentrated by ethanol precipitation and re-suspended in DEPC $H_2O$.

The messenger RNA (mRNA) isolated by the above process contained one or more heavy chain variable domain ($V_H$) coding genes and one or more light chain variable domain ($V_L$)-coding genes. Thus, the mRNA population represents variable region-coding genes which specifically bind to progesterone.

The total RNA was used as a template for the cDNA synthesis by primer extension using Superscript Kit (Life Technologies, Grand Island, N.Y.). Briefly, 7 micrograms (ug) of mRNA was admixed with 60 picomoles (pmol) of a pool of random hexamer oligonucleotide primers provided with the kit, heated to 70° C. for 10 minutes and immediately cooled on ice. Two ul of RNase inhibitor, 10 ul of 5× synthesis buffer, 8 ul of dNTP mix (to give final concentration of 200 uM of each dNTP), 5 ul of 0.1 M DTT, and 1 ul of BRL SuperScript reverse transcriptase (200 U/ul) were admixed, and the reaction was made up to 50 ul with DEPC treated water. The reaction was allowed to proceed at room temperature for 10 minutes and then at 42° C. for 50 minutes. The reaction was terminated by maintaining at 90° C. for 5 minutes and then placing on ice for 10 minutes followed by admixing 1 ul of RNase H and maintaining at 37° C. for 20 minutes. Treatment of the mRNA-cDNA hybrid with RNase H introduces nicks and gaps into the mRNA strand. The remaining RNA serve as primers to produce the second strand of DNA.

The second DNA strand is produced by the addition of *E. coli* DNA polymerase I and incubation at 37° C. to produce second strand DNA. The reaction was then terminated and the ends of the double-stranded DNA were blunted by the addition of Klenow and incubation at 37° C. The Klenow was then heat-killed by incubation at 65° C. for 30 minutes. Following second strand synthesis to form double stranded cDNAs, Not I restriction site linkers were ligated onto the ends of the double stranded cDNAs for subsequent cloning to form a cDNA library. The cDNAs having 5' and 3' Not I linkers were ligated into a Not-1 linearized plasmid Sport 1, which is a useful commercially available cDNA cloning vector (pSport 1, available from Life Technologies). The cDNAs were transformed into *E. coli* DH5alpha competent cells (Life Technologies) according to manufacturer's instructions to form a cDNA library containing $V_H$ and $V_L$-coding sequences.

2. Selection and PCR Amplification of Heavy and Light Chain cDNA Clones

The resultant cDNA library was then screened by hybridization to obtain individual $V_H$ and $V_L$-encoding cDNA clones. Screening was accomplished by separately hybridizing colony lifts with $^{32}$P-labeled specific oligonucleotide primers corresponding to the first constant region of heavy ($C_H1$) and light chains ($C_L$), respectively. Clones for both the heavy chain and light chain thus selected from the cDNA library were mapped and sequenced. Procedures for colony hybridization and sequencing are well known to one of ordinary skill in the art and are described in Current Protocols of Molecular Biology, Ed. Ausebel et al., New York (1989 and current supplements).

The heavy chain variable domain ($V_H$) and a natural linker sequence corresponding to CH1 located 3' to $V_H$ was then amplified from the selected heavy chain clone by polymerase chain reaction (PCR) with oligonucleotide primers that incorporated 5' and 3' restriction sites to allow for subsequent cloning. The 5' primer used to incorporate a 5' Xho I site and amplify the $V_H$ and linker sequence was designated DB31 and had the nucleotide sequence 5'-CAGATCCAGTTGCTCCAGTCTGGACC-3' (SEQ ID NO 16). The 3' primer used to incorporate a 3' Sac I site and amplify the $V_H$ and linker sequence was designated mVHlink and had the nucleotide sequence 5'-CTGGGTCATCTGGAGCTCGGCCAGTGGATAGAC AGATGGGGGTGTCGTTTTGGC-3' (SEQ ID NO 17). Amplification with these primers on the selected $V_H$ cDNA clone resulted in a 400 base pair (bp) product having the respective 5' and 3' Xho I and Sac I restriction cloning sites flanking/$V_H$ and the nucleotide sequence encoding a 19 amino acid linker from CH1. The encoded linker amino acid residue sequence was VTVSSAKTTPPSVYPLAEL (SEQ ID NO 18).

Both the light chain variable domain ($V_L$) and the light chain constant domain ($C_L$) (hereinafter referred to as $V_L/C_L$) were amplified in one continuous sequence from the selected light chain clone with oligonucleotide primers that also incorporated 5' and 3' restriction sites to allow for subsequent cloning. The 5' primer used to incorporate a 5' Sac I site and amplify the $V_L/C_L$ region was designated DB32 and had the nucleotide sequence 5'-TCTACTGAGCTCGTGATGACCCAAACTCCA-3' (SEQ ID NO 19). The 3' primer used to incorporate a 3' Xba I site was designated mouse kappa and had the nucleotide sequence 5'-GCGCCGTCTAGAATTAACACTCATTCCTGTTGAA-3' (SEQ ID NO 20). Amplification with these primers on the selected light chain cDNA library clone resulted in a 380 base pair (bp) product having the respective 5' and 3' Sac I and Xba I restriction cloning sites flanking $V_L/C_L$.

All oligonucleotide primers not provided with kits were either purchased from Research Genetics in Huntsville, Ala. or synthesized on an Applied Biosystems DNA synthesizer, model 381A, using the manufacturer's instruction.

PCR amplification was performed in a 100 ul reaction mixture containing 5 ug of DNA from the selected heavy chain cDNA clone, 200 uM of a mixture of dNTP's, 50 mM KCl, 10 mM Tris-HCl pH 8.3, 15 mM $MgCl_2$, 0.1% gelatin and 2 units of *Thermus aquaticus* (Taq) DNA polymerase (Perkin-Elmer-Cetus, Emeryville, Calif.). The reaction mixture was subjected to 40 cycles of amplification. Each amplification cycle included denaturation at 92° C. for 1 minute, annealing at 52° C. for 2 minutes and polynucleotide synthesis by primer extension (elongation) at 72° C. for 1.5 minutes. The amplified $V_H$-coding DNA sequences were then extracted twice with phenol/chloroform, once with chloroform, ethanol precipitated and are stored at −70° C. in 10 mM Tris-HCl, pH 7.5, and 1 mM EDTA.

The $V_L/C_L$ sequences were also amplified as described above.

3. Insertion of $V_H$ and $V_L$ Coding Sequences into a DNA Expression Vector

To obtain the single chain polypeptide molecules of this invention having the formula V—C where V is a $V_H$ domain attached to a $V_L$ domain comprising an antigen-binding site and where C is a $C_L$ domain that is fused to V, the expression vector constructs described below were made.

a. Preparation of pComb8 Expression Vector

A phagemid vector designated pComb8 allows for both surface display and for the expression of soluble forms of antibody molecules with single or multiple valencies and specificities, and is extensively described by Kang et al., Proc. Natl. Acad. Sci., USA, 88:4363–4366 (1991), the disclosure of which is hereby incorporated by reference.

The pComb8 vector was originally designed for the cloning of combinatorial Fab libraries. For use in this invention, the vector, however, is used as a cloning vehicle independent of the phage surface display system and the ability to produce soluble antibodies. As described herein, the pComb8 vector is used to allow for the directional and in-frame ligation of the $V_H$ and $V_L/C_L$ domain amplified sequences prepared in Example 2 followed by expression of those sequences for secretion into the periplasm of the host bacteria. However, one embodiment of this invention contemplate the use of the advantages of the pComb8 expression vector system in context with the preparation of multivalent and multispecific molecules. Also contemplated is the use of the pComb8 expression vector system for mutagenesis and subsequent selection of antibodies with altered binding affinities or specificities. The expression of the molecules of this invention anchored on the surface of phage facilitated by the phage coat proteins (cp) 8 or 3 is contemplated. Also contemplated is the use of the pComb8 expression vector for use in obtaining soluble forms of the multivalent and multispecific molecules as specified herein. Methods to accomplish these embodiments are described in the references cited above and are well known to one having ordinary skill in the art in phagemid expression systems.

In the pComb vector as originally developed, the Xho I and Spe I restriction sites were provided for cloning complete PCR-amplified heavy chain (Fd) sequences consisting of the region beginning with framework 1 and extending through framework 4. An Aat II restriction site is also present. The presence of the Aat II site allows for the insertion of Xho I/Aat II digests of selected inserts, if required. The Sac I and Xba I sites were provided for cloning PCR amplified antibody light chains. The cloning sites were compatible with previously reported mouse and human PCR primers as described by Huse et al., Science, 246:1275–1281 (1989) and Persson et al., Proc. Natl. Acad. Sci., USA, 88:2432–2436 (1991), respectively. The nucleotide sequence of the pelB, a leader sequence for directing the expressed protein to the periplasmic space, was as reported by Huse et al., supra. Variations on the portion of the antibody which is expressed by the pComb8 expression vector, the spatial arrangement of the antibody portions and the primers used to generate them are also contemplated.

The vector also contained a ribosome binding site as described by Shine et al., Nature, 254:34 (1975). The sequence of the phagemid vector, pBluescript, which includes ColE1 and f1 origins and a beta-lactamase gene, has been previously described by Short et al., Nuc. Acids Res., 16:7583–7600 (1988) and has the GenBank Accession Number 52330 for the complete sequence. Additional restriction sites, Sal I, Acc I, Hinc II, Cla I, Hind III, Eco RV, Pst I and Sma I, located between the Xho I and Spe I sites of the empty vector were derived from a 51 base pair stuffer fragment of pBluescript as described by Short et al., supra. A nucleotide sequence that encodes a flexible 5 amino acid residue tether sequence which lacks an ordered secondary structure was juxtaposed between the Fab and cp8 nucleotide domains so that interaction in the expressed fusion polypeptide was minimized.

Thus, the resultant combinatorial vector, pComb8, as designed for its original intended used, consisted of a DNA molecule having two cassettes to express one fusion polypeptide, Fd/cp8, and one soluble protein, the light chain. The vector also contained nucleotide residue sequences for the following operatively linked elements listed in a 5' to 3' direction: a first cassette consisting of LacZ promoter/operator sequences; a Not I restriction site; a ribosome binding site; a pelB leader; a spacer region; a cloning region bordered by 5' Xho I and 3' Spe I restriction sites; the tether sequence; the sequences encoding bacteriophage cp8 followed by a stop codon; a Nhe I restriction site located between the two cassettes; a second lacZ promoter/operator sequence followed by an expression control ribosome binding site; a pelB leader; a spacer region; a cloning region bordered by 5' Sac I and a 3' Xba I restriction sites followed by expression control stop sequences and a second Not I restriction site.

In the above expression vector, the Fd/cp8 fusion and light chain proteins were placed under the control of separate lac promoter/operator sequences and directed to the periplasmic space by pelB leader sequences for functional assembly on the membrane. Inclusion of the phage f1 intergenic region in the vector allowed for the packaging of single-stranded phagemid with the aid of helper phage. The use of helper phage superinfection allowed for the expression of two forms of cp8. Consequently, normal phage morphogenesis was perturbed by competition between the Fd/cp8 fusion and the native cp8 of the helper phage for incorporation into the virion. The resulting packaged phagemid comprised native cp8, which is necessary for formation of the phage structure, and the encoded antibody, or portion thereof, fusion polypeptide, which is displayed for selection.

1) Preparation of pComb8

A PCR product produced obtained from amplification of M13mp18, a commercially available bacteriophage vector (Pharmacia, Piscataway, N.J.), contained the gene encoding cp8 and had a nucleotide sequence that defines a filamentous bacteriophage coat protein 8 (cp8) membrane anchor domain. Oligonucleotides were designed for amplifying cp8 having cohesive Spe I and EcoR I termini to allow for subsequent ligation into pcomb. The cp8-membrane anchor-encoding PCR fragment was directionally ligated into the pcomb phagemid expression vector at corresponding cohesive termini, that resulted in forming pComb8 (also designated pCombVIII). This vector has been completely described by Kang et al., supra. A similarly prepared vector containing the sequences encoding coat protein 3 described by Barbas et al., Proc. Natl. Acad. Sci., USA, 88:7978–7982 (1991), the disclosure of which is hereby incorporated by reference, is also contemplated for use in this invention.

A preferred phagemid expression vector for use in this invention, designated either pComb2-VIII or pComb2-8, was prepared as described above by directionally ligating the cp8 membrane anchor-encoding PCR fragment into a pComb2 phagemid expression vector via Spe I and EcoR I cohesive termini. The pComb2-8 had only one Spe I restriction site.

B. Ligation of $V_H$ and $V_L/C_L$ Domain Coding Sequences into pComb8

The pComb8 vector prepared above was digested as described herein to allow for the directional insertion and in-frame ligation of the $V_H$ and $V_L/C_L$ PCR amplified products prepared in Example 2. pComb8 was first digested with Xho I and Sac I removing the region between those sites that was used for the expression of Fv on the surface of phage. Into the linearized vector, similarly digested $V_H$ PCR amplified products prepared in Example 2 were directionally ligated to form pComV$_H$link. The resultant pComV$_H$link vector contained, in the 5' to 3' direction after the Xho I site, the $V_H$ domain located 5' to a nucleotide sequence that encoded a 19 amino acid linker sequence listed above. The latter corresponded to the CH1 sequence in the selected cDNA heavy chain clone. The triplet codon encoding the last leucine amino acid residue in the linker comprised the first 3 nucleotides for the Sac I site into which the amplified $V_L/C_L$ domain was ligated as described below wherein the $C_L$ domain was a $C_\kappa$ domain.

The $V_L/C_L$ amplified products were digested with Sac I and Xba I and ligated into a similarly digested pComV$_H$link prepared above to allow for the directional ligation of the $V_L$-encoding sequences 3' to the $V_H$ and linker sequences in pComV$_H$link. Digestion of the pComV$_H$link with Sac I and Xba I removed the control elements for originally expressing the light chain in pComb8. The resultant expression vector designated pComV$_H$K contained in the 5' to 3' direction the in-frame nucleotide sequences for encoding the variable domain of the heavy chain, a 19 amino acid residue linker, the variable domain of the light chain and the constant domain of the light chain. The nucleotide sequence between the 5' Xho I and 3' Xba I sites in the pComV$_H$K vector was 680 bp in length.

An alternative method for directional ligation of the amplified PCR $V_H$ and $V_L/C_L$ products was to ligate the two products via the overlapping Sac I sites to form a 680 bp fragment containing the in-frame nucleotide sequences for encoding the variable domain of the heavy chain, a 19 amino acid residue linker and the variable and constant domains of the light chain. This fragment was then directionally ligated into a the pComb8 expression vector to form pComV$_H$K. Digestion of pComb8 with Xho I and Xba I prior to ligation of the fused PCR products completely removed the region previously used to direct the expression of phage displayed heavy chain and soluble light chain. Therefore, the pComb8 vector was used as an expression vector and not a phagemid display expression vector system.

4. Expression and Selection of Monovalent Single Chain Polypeptide Molecules that Form Bivalent Molecules The resultant pComV$_H$K prepared in Example 3 containing sequences for encoding a single chain fusion polypeptide of this invention containing a $V_H$ domain connected to a $V_L/C_L$ domain by a linker region was then screened to select clones that reacted with progesterone.

For assaying expressed protein by probing colony lifts with an anti-kappa chain antibody, *E. coli* strain XL1-Blue, was first transformed with the pComV$_H$K that contained an ampicillin selectable resistance marker gene. For high efficiency electro-transformation of *E. coli*, a 1:100 volume of an overnight culture of XL1-Blue cells was inoculated into one liter of L-broth (1% Bacto tryptone, 0.5% Bacto yeast extract, 0.5% NaCl). The cell suspension was maintained at 37° C. with vigorous shaking to an absorbance at 600 nm of 0.5 to 1.0. The cell suspension in log phase growth was then harvested by first chilling the flask on ice for 15 to 30 minutes followed by centrifugation in a cold rotor at 4000×g for 15 minutes to pellet the bacteria. The resultant supernatant was removed and the bacterial cell pellet was resuspended in a total of 1 liter of cold water to form a cell suspension. The centrifugation and resuspension procedure was repeated 2 more times and after the final centrifugation, the cell pellet was resuspended in 20 ml of cold 10% glycerol. The resuspended cell suspension was then centrifuged to form a cell pellet. The resultant cell pellet was resuspended to a final volume of 2 to 3 ml in cold 10% glycerol resulting in a cell concentration of 1 to $3 \times 10^{10}$ cells/ml.

For the electro-transformation procedure, 40 ul of the prepared cell suspension was admixed with 1 to 2 ul of expression vector DNA to form a cell-phagemid DNA admixture. The resultant admixture was mixed and allowed to sit on ice for 1 minute. An electroporation apparatus, for example a Gene Pulsar, was set a 25 uF and 2.5 kV. The pulse controller was set to 200 ohms. The cell-DNA admixture was transferred to a cold 0.2 cm electroporation cuvette. The cuvette was then placed in the chilled safety chamber and pulsed once at the above settings. To the pulsed admixture, 1 ml of SOC medium was then admixed and the cells were resuspended with a Pasteur pipette (SOC medium was prepared by admixing 2% Bacto tryptone, 0.5% Bacto yeast extract, 10 mM NaCl, 2.5 mM KCl, 10 mM MgCl$_2$, 10 mM MgSO$_4$, and 20 mM glucose). The cell suspension was then transferred to a 17×100 mm polypropylene tube and maintained at 37° C. for 1 hour. After the maintenance period, the transformed XL1-Blue cells were then plated on ampicillin LB plates for selection of ampicillin resistant colonies containing pComV$_H$K which provided the selectable marker gene.

Ampicillin resistant colonies were first screened by probing colony lifts with a goat anti-mouse kappa chain antibody conjugated to alkaline phosphatase (Southern Biotechnology Associates, Birmingham, Ala.). Anti-kappa antibodies were used in screening as the expressed fusion polypeptide contained the amino acid sequence of the kappa light chain constant domain present in the original DB3 hybridoma cells from which the cDNA library was derived. Standard colony-lift methods including lysis of the colonies and transfer to filter were used to identify colonies expressing the kappa light chain. Filters were blocked in a solution of 1% BSA in PBS for 1 hour before incubation at 25° C. for 2 hours with a 1:1000 dilution of anti-kappa antibody conjugated to alkaline phosphatase in PBS. After reacting, the filters were washed with PBS containing 0.05% Tween 20 before development with substrate (0.1 ml of p-nitrophenyl phosphate at 1 mg/ml in 0.1 M Tris-HCl at pH 9.4 containing 50 mM MgCl$_2$. Ampicillin resistant colonies expressing polypeptides which specifically bound to the anti-kappa antibody were selected for further analysis.

5. Characterization of Single Chain $V_H/V_L/C_L$ Polypeptide Molecules a. ELISA ELISA was performed to determine whether the single chain polypeptide molecules prepared in Examples 3 and 4 containing a $V_H$ domain linked to a $V_L/C_L$ domain (hereinafter referred to as $V_H/V_L/C_L$) via a linker sequence was expressed and if so whether it would immunoreact with the progesterone substrate. The hybridoma cells used to prepared the cDNA library secreted anti-progesterone monoclonal antibodies. For these assays, overnight cultures of XL1-Blue cells (10 ml Luria broth plus carbenicillin at 0.1 mg/ml and 0.2% glucose) carrying the construct for encoding a single chain $V_H/V_L/C_L$ fusion polypeptide of this invention were induced to express the protein by addition of 0.5 mM IPTG. The cells were maintained at 30° C. for a further 3 hours prior to pelleting the cells at 7000 rpm in a JA-20 rotor for 15 minutes at 5° C. The supernatant was decanted and protease inhibitors were added prior to storage at 4° C. In addition to testing the supernatants, bacterial periplasmic extracts, obtained by gently lysis in spheroblast buffer, were also evaluated in ELISA.

Microtitration plates were separately coated with progesterone (progesterone-3-(O-Carboxymethyl)-oxime (Sigma #P4778, Sigma Chemical Co., St. Louis, Mo.) or with a progesterone-BSA conjugate at 0.1 ug/well in 0.1 M Tris-HCl, pH 9.2. After coating, the wells were blocked with 1% BSA in PBS. 100 ul of the $V_H/V_L/C_L$-containing supernatants and periplasmic extracts were separately added to the substrate-coated wells to allow the antigen-binding polypeptides to bind to the substrate. The plates were maintained for 18 hours at 4° C. The plates were then washed with PBS and goat anti-mouse anti-kappa chain alkaline phosphatase conjugate was added (0.1 ml diluted 1:1000 in PBS containing 0.1% BSA). The plates were maintained for 2 hours at room temperature. The plates were then washed in PBS and substrate added (0.1 ml, 1 mg/ml p-nitrophenylphosphate in 0.1 M Tris-HCl at pH 9.5, containing 50 mM $MgCl_2$). After incubation at 37° C. for signal development, the optical densities at 405 nm were determined. Competition assays were performed with the addition of increasing amounts of the progesterone substrate ranging in concentration from zero up to 5 mg/well.

The results of the ELISA showed that the expressed single chain $V_H/V_L/C_L$ fusion polypeptide bound to progesterone in a similar profile to that of the original DB3 monoclonal antibody itself.

b. Determination of Affinity of Single Chain Fusion Anti-Progesterone Antibodies The binding constants of the anti-progesterone single chain $V_H/V_L/C_L$ fusion polypeptide are determined by competitive ELISA. Briefly, wells of a microtitration plate are coated at 4° C. with 50 ul of 100 ug/ml progesterone-BSA conjugate in PBS. The wells are washed twice with water and blocked with 1% w/v BSA in PBS at 37° C. for 1 hour. The supernatants or periplasmic extracts prepared above are mixed with progesterone-BSA in PBS with BSA (0.1% w/v), and maintained in the wells at 37° C. for 2 hours. The plates are washed with PBS-Tween (0.05% v/v), and goat anti-mouse kappa-chain alkaline phosphatase conjugate (Southern Biotech) and maintained for 1 hour at 37° C. The plates are washed as before and substrate is admixed (0.1 ml, p-nitrophenyl phosphate at 1 mg/ml in 0.1 M Tris, pH 9.4 containing 50 mM $MgCl_2$). After maintenance at 25° C. for 60–180 minutes, the absorbance is read at 405 nm. Apparent affinities are determined as the reciprocal of the substrate concentration required to inhibit 50% of the maximal binding in a competitive ELISA. This is a close approximation to the affinity.

c. Gel Electrophoresis of *E. coli* Periplasmic Extracts Containing the Single Chain $V_H/V_L/C_L$ Fusion Polypeptide In order to determine the structural aspects, specifically the valency, of the expressed anti-progesterone single chain $V_H/V_L/C_L$ fusion polypeptides characterized above, gel electrophoresis was performed under both reducing and non-reducing conditions by SDS-PAGE gel analysis. Periplasmic extracts prepared in Example 5a were immunoprecipitated by specifically binding to progesterone and the immunoprecipitates electrophoresed against control monomeric and dimeric Fabs, respectively, Fab' and (Fab')$_2$. Monomeric Fab' having only one $V_H/V_L$ domain migrated under reducing conditions at 25 kD (kilodaltons) while the dimeric structure migrated at 50 kD. Similarly, reduced periplasmic extracts containing the $V_H/V_L/C_L$ fusion polypeptide migrated at 37.5 kD while the same extracts run under non-reducing conditions migrated at 75.0 kD. Thus, the reactive form of the anti-progesterone single chain $V_H/V_L/C_L$ fusion polypeptide of this invention was a dimer. This structure is also referred to as being bivalent existing with 2 separate subunits of variable heavy and light chain antigen binding domains.

The dimerized structure has been shown to be the result of a disulfide bond formed between single natural cysteine residues on two separate light chain constant domain fusion polypeptides. The formation of the disulfide bond has been shown to occur in the periplasm of the *E. coli* host following expression of the individual fusion polypeptides. The bivalent anti-progesterone $V_H/V_L/C_L$ fusion polypeptide of this invention is the first recombinant molecule discovered that contains the following elements: variable domains of both heavy and light chains linked together by a natural linker of the heavy chain constant domain; variable domains fused to a kappa light chain constant domain; dimerization of two individual fusion polypeptides through a disulfide bond linking two separate kappa light chain constant domains; and a bivalent polypeptide that has the ability to bind to a preselected antigen.

This prototype bivalent or dimeric polypeptide only has one antigen-binding specificity. As described below, the methods of this invention have been further adapted for use in generating bivalent polypeptides that exhibit more than one antigenic specificities, in particular two and three specificities. Bivalent polypeptides were also generated in a single chain construct where two single chain variable domains were joined together through a constant domain region. Dimers forming between two of these bivalent single chain constructs resulted in the formation of a tetravalent antibody. In addition, the methods of this invention can be adapted to produce antigen-binding polypeptides that exist in multimeric forms that exhibit multiple specificities. Moreover, the methods of this invention can be used to obtain constructs that encode altered rearrangements of the various domains of the fusion polypeptides. For example, the heavy and light chain variable domains can be inverted such that the light chain is located at the amino terminus of the protein and the heavy chain variable domain is located at the carboxy terminus of the light chain fused to a constant domain. Further, the methods of this invention provide for constructs that have interchangeable heavy and light chain constant domains that provide for distinct multivalent forms of antigen-binding polypeptides.

6. Preparation of a Single Chain Bispecific Bivalent Antigen-Binding Polypeptide The method described herein was used to generate a bispecific antigen-binding polypeptide on a single chain construct. The construct was designed to incorporate two distinct antigen-binding specificities into one single chain fusion polypeptide such that when the individual polypeptides dimerized through a disulfide bond, a bispecific tetravalent polypeptide would be formed. In the Examples described below, a DNA construct encoding the heavy and light chain variable domains that bind the antigen dinitrophenol (DNP) was used to make one antigen-binding encoding domain of the single chain polypeptide. The other DNA construct used for providing the other antigen-binding specificity encoded a recombinant Fab directed against nitrophenylphosphonamidate (NPN). As described below, the anti-NPN Fab-encoding construct was used to construct a DNA sequence for encoding an anti-NPN single chain polypeptide consisting of heavy and light chain variable domains operationally attached to the anti-NPN kappa light chain, hereinafter referred to as WAT 2 having a $V_H/V_L/C_L$ domain.

a. Preparation of an Anti-NPN Single Chain $V_H/V_L/C_L$-Encoding Construct

The anti-NPN Fab clone 2b, a Fab in the lambda ZAP vector system previously described by Huse et al., *Science*, 246:1275–1281 (1989), was used to generate a single chain $V_H/V_L/C_L$-encoding DNA construct designated WAT 2. The WAT 2 construct was then ligated into an expression vector as described below along with an anti-DNP-encoding single chain $V_H/V_L$ construct to form a single chain bispecific molecule.

The WAT 2 construct was made using PCR amplification of the variable heavy chain in clone 2b. PCR was performed with 1 ng of clone 2b as the template with 100 ng of the oligonucleotide primers, T3 and mVHlink, having the respective nucleotide sequences, 5'-ATTAACCCTCACTAAAG-3' (SEQ ID NO 21) and 5'-CTGGGTCATCTGGAGCTCGGCCAGTGGATAGAC AGATGGGGGTGTCGTTTTGGC-3' (SEQ ID NO 17). The 3' mVHlink primer was used to incorporate a 3' Sac I site and amplify the $V_H$ and linker sequence as described in Example 2. The other reagents required for PCR described in Example 2 were added to the reaction admixture and the amplification was performed for 30 cycles with each cycle consisted of 1 minute at 94° C., 1 minute at 52° C., and 1 minute at 72° C.

The resultant amplification product consisting of 550 bp encoding the variable domain of the heavy chain was digested with Sac I and then cloned back into the template clone 2b, previously digested with Sac I. Digesting clone 2b with Sac I removed the original 2b heavy chain consisting of variable and constant domains and allowed the amplified heavy chain variable domain to be ligated back in 5' to the light chain cassette that consisted of the light chain variable domain operationally and in-frame linked with the kappa light chain constant domain.

The correct orientation of the religated amplified heavy chain was determined by filter lift screening with an anti-kappa antibody as described in Example 4. Three clones having a DNA construct for encoding the $V_H/V_L/C_L$-anti-NPN single chain polypeptide were selected by the screening protocol. The presence of the construct was further identified by restriction mapping showing that all 3 clones had the correct insert. The resultant WAT 2 designated clone was shown to bind to NPN in ELISA assays performed as described in Example 5a with NPN used as the substrate. The WAT 2 construct was then used in the construction of the single chain bispecific antibody having both NPN and DNP antigen specificities as described below.

b. PCR Amplification of WAT 2 $V_H/V_L/C_L$-Encoding Construct

The primer, mk3' Aat II, was designed to amplify the WAT 2 $V_H/V_L/C_L$-encoding construct. This primer primed at the 3' end of the construct where the Xba I site and stop codons are. The primer removed the stop codon and replaced the Xba I site with an Aat II site. The mk3' Aat II primer had the nucleotide sequence 5'-AATATCGACGTCACCTCCACACTCATTCCTGTT GAA-3' (SEQ ID NO 22). For the PCR amplification, 1 ng of WAT 2 was used as the template along with 100 ng of the T3 primer listed in Example 6a and the mk3' Aat II primer. PCR was performed as described in Example 6a.

In addition to amplification of WAT 2, the primer pairs above were used in separate amplifications with templates vk/5 and DB3 to form similar amplification products anti-progesterone $V_H/V_L/C_L$-encoding constructs. These amplification products were used with the anti-DNP $V_L/V_H$ construct to form separate bispecific single chain polypeptides that would have antigen binding specificities to DNP and progesterone.

In each amplification, the 1.2 kb PCR products were excised from an agarose gel and purified by GeneClean (BIO101, San Diego, Calif.). The purified PCR products were then digested with Aat II and then Xho I for insertion into the pComb8 expression vector as described below.

c. Production of the Bispecific Single Chain-Encoding DNA Constructs

The complete construct designated U7.6 that encoded an anti-DNP $V_L/V_H$ single chain polypeptide was first ligated into the Xho I and BamH I restriction sites of pComb8 prepared in Example 3. Restriction mapping identified 4 clones having the anti-DNP-encoding insert, including clone pGB 42. The clone designated pGB 42 containing the anti-DNP variable domain construct was then digested with Aat II and Xho I followed by (calf intestinal alkaline phosphatase) CIAP treatment to allow for ligation of the similarly digested anti-NPN or anti-progesterone single chain $V_H/V_L/C_L$-encoding constructs prepared in Example 6b. Anti-DNP-encoding clones having the newly inserted $V_H/V_L/C_L$-encoding constructs were identified by filter lifts with an anti-kappa chain antibody as described in Example 4.

Thus, the resultant bispecific single chain constructs encoded a polypeptide having one DNP antigen binding domain with a second antigen binding domain against either NPN or progesterone. In both polypeptides, the single chain polypeptide was comprised of the following immunoglobulin domains operationally fused in the amino to carboxy terminus direction: the variable heavy domain attached to the amino terminus of the variable light chain domain fused to the constant light chain domain encoded by either the progesterone- or NPN-specific constructs operationally fused by the Aat II restriction site to the variable light chain connected to the variable heavy chain domain encoded by the DNP-specific constructs.

In formula shorthand, the single chain polypeptide consisted of $V_H$—$V_L$—$C_L$—$V_L$—$V_H$, where the amino variable domain recognized either NPN or progesterone and the carboxy terminal variable domain recognized DNP. The two antigen binding domains were separated by the constant domain of the light chain derived from either the NPN or progesterone constructs. The formulation can be reduced to V—X—V where V is both of the antigen-binding domains and X is the light chain constant domain. The methods of this invention can be used to generate bispecific single chain polypeptides of this invention where the variable domain heavy and light chain domains are inverted in amino to carboxy terminus order. In addition, the methods used herein can be used to prepared single chain bispecific polypeptides having a constant heavy chain domain instead of the light chain.

d. Expression and Characterization of the Bispecific Single Chain Polypeptides

Expression of the bispecific constructs prepared above was accomplished as described in Example 4. Following expression, ELISA was performed as described in Example 5a against each of the antigens recognized by the individual antigen binding domains in the bispecific constructs.

In Example 5, evidence was provided that showed that single chain polypeptides having only one antigen binding domain that bind to progesterone exist as dimeric or bivalent polypeptides through the formation of a disulfide bridge between separate kappa light chain constant domains on two monomeric polypeptides. Since the bispecific single chain polypeptides prepared herein also have a light chain constant domain on each polypeptide, the bispecific polypeptides are expected to form similar dimerized structures. The resulting dimer consists of 4 antigen-binding domains, two that recognize one antigen, such as NPN or progesterone, and two that recognize the other antigen, DNP. The dimer thus has a tetravalent structure with bispecificity against preselected antigens.

7. Preparation of a Anti-CD3 and Anti-CD4 Bispecific Bivalent Antigen-Binding Polypeptide The method described herein was used to generate an additional bispecific bivalent antigen-binding polypeptide on a single chain construct. The construct was designed to incorporate T cell CD3 and CD4 antigen-binding specificities into one single chain fusion polypeptide such that when the individual polypeptides dimerized through a disulfide bond, a bispecific tetravalent polypeptide would be formed. In the Examples described below, a DNA construct encoding the heavy and light chain variable domains from an OKT3 recombinant Fab that binds the antigen CD3 was used to make one antigen-binding encoding domain of the single chain polypeptide. The other DNA construct designated OKT4 used for providing the other antigen-binding specificity encoded a recombinant Fab directed against CD4.

The murine OKT3 and OKT4 hybridomas are available from the American Type Culture Collection and are designated CRL 8001 and CRL 8002, respectively. The nucleotide sequence of the DNA constructs used herein as templates to generate DNA constructs encoding the heavy and light chain variable and constant domains were changed from amino acid residues encoded by mouse immunoglobulins to amino acid residues encoded by human immunoglobulins as described in Kabat et al., *Sequences of Immunological Interest,* National Institutes of Health, Bethesda, Md., (1987), in order to humanize the murine antibody. These changes were made to decrease the potentially immunogenic effects when introduced into humans during immunotherapy.

A. Preparation of an Anti-CD3 Single Chain $V_H/V_L/C_L$-Encoding Construct

The anti-CD3 antibody that forms the basis for the single chain construct was originally expressed in a commercially available eucaryotic expression vector, pSG5 (Stratagene, La Jolla, Calif.), as separate chains in 2 different clones designated pSG5 221C for the light chain and pSG5 209 for the heavy chain of the anti-CD3 antibody OKT3. pSG5 221C and pSG5 209 were prepared and provided by Dr. L. Joliff (Johnson & Johnson, N.J.). The single chain monospecific and monovalent anti-CD3 $V_H/V_L/C_L$-encoding construct was first prepared in pSG5. Because of the usage of restriction sites, ligation of the heavy chain and linker sequence into the light chain vector was not possible. Therefore, the single chain construct was achieved as described below by a three-way ligation of the kappa chain constant domain digested with BamH I and EcoR V, the heavy chain and linker domain PCR product digested with EcoR V and EcoR I, and the pSG5 digested with EcoR I and BamH I.

The heavy chain variable domain including a linker sequence was first amplified from the OKT3 antibody-encoding construct using 1 ng of pSG5 209 as a template and 100 ng of each of the oligonucleotide primers, OKT3 H1 and OKT3 H2, having the respective nucleotide sequences 5'-TCCTGGGAAAGATTGTAATACGAC-3' (SEQ ID NO 23) and 5'-CATCTGGATATCCGCCAGGGGGAAGACGGA-3' (SEQ ID NO 24). The resultant PCR product having 500 bp was digested with EcoR I and EcoR V for ligation into pSG5.

The kappa chain consisting of the variable and constant domains was digested out of pSG5 221C with BamH I and EcoR V. The pSG5 expression vector was digested with EcoR I and BamH I followed by (CIAP) treatment.

The three-way ligation was carried out with the digested heavy chain PCR product, the kappa light chain and the vector. Clones with the correct insert were identified by restriction mapping with EcoR I that cuts out the 1.2 kb $V_H/V_L/C_L$-encoding insert. Five clones, designated pHI 40, 44, 45, 48 and 49, were found to contain the single chain construct.

For expression of the resultant monospecific monovalent single chain anti-CD3 polypeptide, COS cells were transfected with pHI 45 using the calcium phosphate precipitation method. PHI 45 expresses a humanized OKT3 single chain polypeptide comprosed of the variable heavy chain and kappa light chain constant domain. Protein synthesis was monitored by labeling with $^{35}$S-methionine. Cell lysates and supernatants were both immunoprecipitated with CD3 antigen. The supernatant and lysates of the test transfection and the negative control were electrophoresed on protein gels under both reducing and non-reducing conditions. Methods for transfection of DNA plasmids into mammalian cells, maintenance of mammalian cells, labeling of cells with $^{35}$S-methionine, immunoprecipitation and gel electrophoresis are well known to one of skill in the art.

The reducing gel indicated that a polypeptide of the correct size, approximately 37.5 kb, was produced by the COS cells containing the test DNA but not by the negative control cells. The non-reducing gel indicated that the single chain polypeptide existed in a dimerized form as a result of a disulfide bond between two cysteine residues from each of the light chain constant domains. Thus, the anti-CD3 single chain polypeptide formed a bivalent antigen binding molecule similar to the anti-progesterone molecule described in Example 5.

B. ELISA

The anti-CD3 single chain polypeptide expressed and isolated as described above is then assayed for binding to CD3 in an ELISA assay. Microtitration plates are separately coated with CD3 or with a CD3-BSA conjugate each at 0.1 ug/well in 0.1 M Tris-HCl, pH 9.2. After coating, the wells were blocked with 1% BSA in PBS. 100 ul of the $V_H/V_L/C_L$-containing immunoprecipitates are separately added to the substrate-coated wells to allow the antigen-binding polypeptides to bind to the substrate. The plates are maintained for 18 hours at 4° C. The plates are then washed with PBS and goat anti-human kappa chain alkaline phosphatase conjugate was added (0.1 ml diluted 1:1000 in PBS containing 0.1% BSA). The plates are maintained for 2 hours at room temperature. The plates are then washed in PBS and substrate added (0.1 ml, 1 mg/ml p-nitrophenylphosphate in 0.1 M Tris-HCl at pH 9.5, containing 50 mM $MgCl_2$). After incubation at 37° C. for signal development, the optical densities at 400 nm are determined. Competition assays are performed with the addition of increasing amounts of the respective substrates ranging in concentration from zero up to 5 mg/well.

The results of the ELISA show that the expressed single chain $V_H/V_L/C_L$ fusion polypeptide binds to CD3 in a similar profile to that of the original OKT3 monoclonal antibody itself.

C. Preparation of a Monospecific Anti-CD3 Tetravalent Antigen Binding Polypeptide The sequences encoding the variable heavy and light chain domains present in the single chain anti-CD3 polypeptide prepared in Example 7a are duplicated and fused to the 3' end of the single chain construct to form a bivalent single chain anti-CD3 construct having two antigen binding domains flanking an internal light chain constant domain. This structure is similar to that described in Example 6. Since a dimer is formed between the kappa constant domains, a bivalent single chain polypeptide forms a dimeric structure through kappa chain interactions resulting in the formation of a tetravalent polypeptide that binds CD3. Thus, the polypeptide has 4 *binding domains to interact with CD*3 that provides for a higher affinity binding reaction.

The resultant tetravalent anti-CD3 polypeptide, upon binding to T cells, cross-links the CD3 antigen on the T cell surface and activates the T cell.

In order to construct a bivalent anti-CD3 DNA molecule, the stop codons at the end of the light chain constant domain in the pHI 45 construct were removed. To remove the stop codons, primers were designed to amplify the complete $V_H/V_L/C_L$-encoding insert. The 3' primer, BG1, was designed to remove the stop codon, add a three amino acid Gly-Gly-Ser linker and maintain the BamH I site. BG1 had the nucleotide sequence 5'-AACCTGGGATCCGCCCCCACACTCTCCCCTGTT GAAGAAGCTCTT-3' (SEQ ID NO 25). The OKT3 H1 primer listed in Example 7a was used as the 5' primer in the amplification reactions. The amplification was performed with 1 ng of pHI 45 prepared in Example 7a as the template with 100 ng of each primer. PCR was performed as described previously. The resultant 1.2 kb PCR product was-gel purified and digested with EcoR I and BamH I.

The digested PCR product was then ligated into pSG5 that was previously digested with the same enzymes so that the insert was directionally ligated into the vector. The presence of the insert was identified by restriction mapping. Twelve clones, designate OKT3 tet/A1–A12, were identified with the correct insert.

The next step was the amplification of the variable heavy and light chain domains from the pHI 45 vector having the single chain construct. For this amplification, the 5' and 3' primer pair, respectively, BG2 and BG3, were used. BG2 introduced a BamH I site upstream of the variable heavy chain domain and the BG3 3' primer introduced a BamH I and a stop codon downstream of the variable light chain domain. The primers BG2 and BG3 had the respective nucleotide sequences 5'-TGTGGGGGCGGATCCCAGGTTCAGCTGGTGCA GTCTGGAGGAGGA-31' (SEQ ID NO 26) and 5'-TATAGGATCCTATTATCTTGTGATCTGCAGCTTTG-3' (SEQ ID NO 27). A 700 bp PCR product of the variable heavy and light chain domain ($V_H/V_L$) resulted from the amplification reaction.

To form a bivalent anti-CD3 single chain polypeptide, the OKT3 tet/A1 clone was digested with BamH I and CIAP treated. The $V_H/V_L$ digested PCR product prepared above was then ligated into the digested OKT3 vector containing a single chain monovalent construct. The ligation resulted in the formation of a construct that encoded a bivalent anti-CD3 single chain polypeptide that was comprised of two antigen binding variable domains separated by a constant light chain domain.

Expression of the bivalent construct in COS cells results in a dimeric polypeptide consisting of two single chain polypeptides joined by a disulfide bond through cysteine residues in the kappa constant domain. The resulting dimeric polypeptide thus has 4 antigen binding domains, i.e., is tetravalent, and 2 light chain constant domains. The 4 antigen binding domains bind to the same antigen, therefore, the resulting dimeric polypeptide is monospecific. The dimerized polypeptide has a molecular weight of approximately 145 kD when electrophoresed under non-reducing conditions. When electrophoresed under reducing conditions, the molecule migrates as a monomer having a molecular weight of approximately 72.5 kD.

D. Preparation of a Bispecific Anti-CD3 and Anti-CD4 Tetravalent Antigen Binding Polypeptide Separate constructs that encoded both anti-CD3 and anti-CD4 bivalent single chain polypeptides were used to create a construct for the expression of a bivalent bispecific single chain polypeptide. The construct was prepared by using overlap PCR.

The humanized OKT4 anti-CD4 antibody constructs were prepared and provided by Dr. L. Joliff (Johnson & Johnson) in the form of expression plasmids pSG5 LDR3Q (light chain) and pSG5 HCDR11-R19 (heavy chain).

Since the humanized light and heavy chains of OKT4 anti-CD4 construct were in separate plasmids, pSG5 LDR3Q and pSG5 HCDR11-R19, respectively, separately PCR amplifications were performed to isolate the individual domains and incorporate restriction sites for subsequent overlap PCR. The $V_L$ domain was amplified from pSG5 LDR3Q using the 5' and 3' primer pair, BG4 and BG5, having the respective nucleotide sequences 5'-GAGTGTGGAGGGGGTTCTGATATCCAGATGACA CAGTCTCCT-3' (SEQ ID NO 28) and 5'-CTGAACCTGAGATCCCCCGAAGATGAAGACAG ACGGCGCCGCCACAGT-3' (SEQ ID NO 29). The $V_H$ domain was amplified from pSG5 HCDR11-R19 using the 5' and 3' primer pair, BG6 and BG7, having the respective nucleotide sequences 5'-GTCTTCATCTTCGGGGGATCTCAGGTTCAGCTG GTGGAGTCT-3' (SEQ ID NO 30) and 5'-CATCTGGATATCAGAACCCCCTCCACACTCTCCC CTGTTGAAGCTCTT-3' (SEQ ID NO 31).

PCR was performed as previously described. Both resultant products were 350 bp in length. After gel purification, the products were mixed together and used as a template for overlap PCR using BG4 and BG7 as primers to anneal the $V_L$ and $V_H$ together. BG7 encoded a BamH I site facilitating the ligation of the resultant overlap PCR $V_L/V_H$ product back into the pSG5 expression vector.

Using the OKT3 H1 and BG8 as 5' and 3' primers, respectively, the anti-CD3 encoding $V_H/V_L/C_L$ construct prepared in Example 7b was amplified. The sequence of the OKT3 H1 primer was previously listed. BG8 had the nucleotide sequence 5'-CATCTGGATATCAGAACCCCCTCCACACTCTCC CCTGTTGAAGCTCTT-3' (SEQ ID NO 32). PCR was performed as previously described.

In order to make the anti-CD3 and anti-CD4-encoding bivalent construct, overlap PCR was performed with OKT3 H1 and BG7 as primer pairs with a mixture of the overlap OKT4 $V_L/V_H$ amplification product and OKT3 $V_H/V_L/C_L$ amplification product. The resultant amplification product of 2 kb is then ligated into pSG5 using EcoR I and BamH I restriction sites to form an expression vector construct that will provide for the expression of a bivalent bispecific polypeptide. The resultant expressed bivalent bispecific polypeptide forms a dimer with an identical polypeptide resulting in the formation of a tetravalent bispecific polypeptide that binds both CD3 and CD4 on the surface of T cells. The binding interactions then result in the activation of T cells via the cross-linking of the T cell surface antigens.

8. Preparation, Purification and Characterization of a Anti-CD3 with Kappa Light Chain Constant Region and Anti-CD4 with Lambda Light Chain Constant Region Bispecific Divalent Antigen Binding Polypeptide The separate constructs that encoded both anti-CD3 and anti-CD4 monovalent single chain polypeptides are again combined to create a construct for the expression of a bispecific single chain polypeptide. However, in this example, the anti-CD3 and anti-CD4 light chain constant regions are $C_\kappa$ and $C_\lambda$, respectively, and the method of inserting the anti-CD3 and anti-CD4 $V_H/V_L/C_L$ constructs into a single expression vector is different. First, the anti-CD3 $V_H/V_L/C_\kappa$ construct is inserted into the pCMV vector from the pSG5 vector. Secondly, the anti-CD4 $V_H/V_L/C_\lambda$ is generated by PCR, inserted into the pCRII vector, and subsequently inserted into the pCMV vector containing the anti-CD3 $V_H/V_L/C_\kappa$ construct.

The anti-CD3 $V_H/V_L/C_\kappa$ and anti-CD4 $V_H/V_L/C\lambda$ constructs are expressed as separate polypeptides from separate cistrons in the pCMV vector. The anti-CD3 cistron is derived from the pSG5 vector and comprises the SV40 promoter, anti-CD3 $V_H/V_L/C_\kappa$ construct and polyadenylation signal which are operatively linked. The anti-CD4 cistron is derived from the pCMV vector and comprises the a promoter, the anti-CD4 $V_H/V_L/C\lambda$ construct and a polyadenylation signal which are operatively linked for expression of the anti-CD4 construct.

A. Preparation of an Anti-CD4 $V_H/V_L/C_\lambda$-Encoding Construct

Separate PCR amplifications are performed to isolate the individual $V_H$ and $V_L$ domains from the DNA encoding the humanized heavy and light chains of anti-CD4 contained in the separate plasmids, pSG5 LDR3Q and pSG5 HCDR11-R19, respectively. The PCR primers incorporate restriction sites for insertion into an expression vector and complementary nucleotide sequences for the overlap PCR reaction. The $V_L$ domain is amplified from pSG5 LDR3Q using the 5' and 3' primer pair, GL-3 and GL-4, having the respective nucleotide sequences
5'-CCCCCTGGCGGGGGATATCCAGATGACACAGTC TCC-3' (SEQ ID NO 33) and 5'-GCAGCTTGGGCTGTGTGATCTGCAGCTTTGTTC CCTGTCCG-3' (SEQ ID NO 34). The $V_H$ domain is amplified from pSG5 HCDR11-R19 using the 5' and 3' primer pair, GL-1 and GL-2 having the respective nucleotide sequences
5'-AGAATGCGGCCGCCACCATGGAATGGAGCTGG GTC-3' (SEQ ID NO 35) and 5'-CTGGATATCCCCCGCCAGGGGGAAGACGGATG GGCCC-3' (SEQ ID NO 36).

An additional PCR amplification is performed to isolate the $C_\lambda$ domain from the DNA encoding a lambda light chain contained in a separate plasmid, pLambda, containing the human SpA 3-08 hu lambda Fab clone, provided by Dr. Greg Silverman (University of California at San Diego, Calif.). The PCR primers incorporate restriction sites for subsequent insertion into an expression vector and introduce complementary nucleotide sequences for the overlap PCR reaction. The $C_\lambda$ domain is amplified from pLambda using the 5' and 3' primer pair, GL-5 and GL-6, having the respective nucleotide sequences
5'-AAGCTGCAGATCACACAGCCCAAGGCTGCCCC CTCGGTC-3' (SEQ ID NO 37) and 5'-AAATGCGGCCGCTTATGAACATTCCGTAGGGGC AACTGTCTTCTCC-3' (SEQ ID NO 38).

PCR is performed in three separate reactions as previously described. The resultant products of each of the three separate amplifictaions are approximately 400 bp in length. After gel purification, the products are mixed together and are used as a template for overlap PCR using GL-1 and GL-6 as primers to join the $V_L$, $V_H$ and $C_\lambda$ together and form the anti-CD4 $V_L/V_H/C_\lambda$ construct. The resultant PCR product consisting of the anti-CD4 $V_L/V_H/C_\lambda$ construct is approximately 1.2 kilobase pairs in length.

B. Preparation and Insertion of an Anti-CD3 $V_H/V_L/C_L$-Encoding Construct into pCMV Expression Vector The anti-CD3 $V_H/V_L/C_L$-Encoding Construct was prepared as described above for anti-CD4 into a PCMV expression vector using PCR and the pSG5 221C and pSG5 209 vectors described earlier as the source of $V_H$, $V_L$, and $C_L$.

C. Insertion of Anti-CD4 Single Chain $V_H/V_L/C_\lambda$-Encoding Construct into pCRII and Subsequent Insertion into pCMV Vector Containing Anti-CD3 Single Chain $V_H/V_L/C_\kappa$-Encoding Construct The anti-CD4 $V_L/V_H/C_\lambda$ construct is first inserted into the pCRII vector (Invitrogen, San Diego, Calif.) which has been digested with Not I. The anti-CD4 $V_L/V_H/C_\lambda$ construct is then removed from the pCRII vector by digestion with BamH I and inserted into the pCMV vector containing the anti-CD3 $V_H/V_L/C_\kappa$ construct prepared as described in Example 8A which has been similarly digested.

Thus, the resultant single chain constructs each encode a polypeptide having either an anti-CD3 or anti-CD4 antigen binding domain and a light chain constant region. In both polypeptides, the single chain polypeptide is comprised of the following immunoglobulin domains operationally fused in the amino to carboxy terminus direction: the variable heavy domain attached to the amino terminus of the variable light chain domain fused to the light chain constant domain ($V_H/V_L/C_L$). In the polypeptide having an anti-CD3 antigen binding domain, the light chain constant domain is a kappa light chain constant domain. In the polypeptide having an anti-CD4 antigen binding domain, the light chain constant domain is a lambda light chain constant domain.

In formula shorthand, one of the single chain polypeptides consists of $V_H/V_L/C_{78}$, where the amino variable domain specifically binds CD3 and the light chain constant domain is kappa and the other single chain polypeptide consists of $V_H/V_L/C_\lambda$, where the amino variable domain specifically binds CD4 and the light chain constant domain is lambda. The methods of this invention can be used to generate single chain polypeptides where the variable domain heavy and light chain domains are inverted in amino to carboxy terminus order. In addition, the methods used herein can be used to prepared single chain polypeptides having a constant heavy chain domain instead of the light chain. When the single chain polypeptide has a constant light chain domain, the light chain constant domain can be either kappa or lambda.

D. Expression and Sequential Purification of Anti-CD3 with Kappa Light Chain and Anti-CD4 with Lambda Light Chain Bispecific Bivalent Polypeptides The single chain anti-CD3 and anti-CD4 polypeptides are coexpressed and linked together in mammalian cells to form bispecific bivalent polypeptides by the formation of disulphide bonding. For expression of the resultant bispecific anti-CD3 with kappa light chain and anti-CD4 with lambda light chain polypeptides, COS cells are transfected and protein synthesis monitored as described in Example 7A.

Anti-CD3 with kappa light chain and anti-CD4 with lambda light chain divalent antigen binding polypeptides are isolated from transfected COS cells by sequential purification using an antibody which specifically binds to the kappa light chain constant domain and then using an antibody which specifically binds to the lambda light chain constant domain. The mammalian cells expressing the polypeptides are lysed under conditions which maintain the ability of the constant regions of the polypeptides to bind to their respective anti-immunoglobulin antibodies.

The methods used to purify the anti-CD3 and anti-CD4 divalent antigen binding polypeptides of this invention are to first bind the polypeptides to a first anti-immunoglobulin antibody which specifically binds to the kappa light chain constant domain, thereby isolating polypeptides containing the kappa light chain constant domain. Nonspecifically bound molecules are removed in a wash step with a suitable buffer. The specifically bound polypeptides containing the kappa light chain constant domain are then eluted and bound to a second anti-immunoglobulin antibody which specifically binds to the lambda light chain constant domain, thereby isolating polypeptides containing the lambda light chain domain. Nonspecifically bound molecules are removed in a wash step with a suitable buffer and the specifically bound polypeptides containing the lambda light chain constant domain are eluted. Polypeptides which are sequentially purified as described above are those polypeptides which contain both the kappa and lambda light chain constant regions and are thus bispecific bivalent polypeptides containing anti-CD4 $V_H/V_L/C_\lambda$ anti-CD3 $V_H/V_L/C_\kappa$.

Alternatively, polypeptides containing the kappa and lambda constant regions can be sequentially purified by first binding to an anti-immunoglobulin antibody which specifically binds the lambda light chain constant region and then binding the polypeptides containing lambda light chain constant regions to an antibody which specifically binds the kappa light chain constant region. Polypeptides which are purified by either of these methods contain both the kappa and lambda light chain constant regions. Thus, this invention provides a means to prepare and purify bispecific bivalent polypeptides having two antigen binding sites which specifically bind two different antigens.

E. Characterization of Anti-CD3 with Kappa Light Chain and Anti-CD4 with Lambda Light Chain Bispecific Bivalent Polypeptide The anti-CD3 with kappa light chain and anti-CD4 with lambda light chain bispecific bivalent polypeptide isolated as described in Example 8D by sequential purification is then analyzed to determine the structural aspects of the expressed polypeptides.

1) Gel Analysis of Polypeptides

In order to verify the valency of the expressed anti-CD3 $V_H/V_L/C_\kappa$ and anti-CD4 single chain $V_H/V_L/C_\lambda$ polypeptides purified above, gel electrophoresis is performed under both reducing and non-reducing conditions by SDS-PAGE gel analysis. Sequentially purified proteins prepared in Example 8D are electrophoresed against control monomeric and dimeric Fabs, respectively, Fab' and (Fab')$_2$. Monomeric Fab' having only one $V_H/V_L$ domain migrates under reducing conditions at 25 kD while the dimeric structure migrates at 50 kD. Similarly, reduced purified protein containing the anti-CD3 $V_H/V_L/C_\kappa$ polypeptide and anti-CD4 $V_H/V_L/C_\lambda$ polypeptide migrate at 37.5 kD while the same extracts run under non-reducing conditions migrate at 75.0 kD. Thus, the sequentially purified form of the anti-CD3 $V_H/V_L/C_\kappa$ polypeptide and anti-CD4 $V_H/V_L/C_\lambda$ polypeptide of this invention is a dimer. This structure is also referred to as being bivalent existing with 2 separate subunits of variable heavy and light chain antigen binding domains and as being bispecific existing with variable heavy and light chain antigen binding domains which specifically bind two different antigens.

The dimerized structure is the result of disulfide bond formation between single natural cysteine residues on kappa and lambda light chain constant domain polypeptides.

Bivalent polypeptides are also generated in a single chain construct where two single chain variable domains are joined together through a constant domain region. Dimers forming between two of these bivalent single chain constructs results in the formation of a tetravalent antibody. Thus, the methods of this invention can be adapted to produce antigen-binding polypeptides that exist in multimeric forms that exhibit multiple specificities. Moreover, the methods of this invention can be used to obtain constructs that encode altered rearrangements of the various domains of the fusion polypeptides. For example, the heavy and light chain variable domains can be inverted such that the light chain is located at the amino terminus of the protein and the heavy chain variable domain is located at the carboxy terminus of the light chain fused to a constant domain ($V_L/C_L/V_H$). Further, the methods of this invention provide for constructs that have interchangeable heavy and light chain constant domains that provide for distinct multivalent forms of antigen-binding polypeptides.

2) ELISA

The binding specificities of the anti-CD3 $V_H/V_L/C_\kappa$ and anti-CD4 $V_H/V_L/C_\lambda$ polypeptide purified as described above are determined in an ELISA assay as described in Example 7B with CD3 and CD4 as the antigens.

The anti-CD3 $V_H/V_L/C_\kappa$ and anti-CD4 $V_H/V_L/C_\lambda$ polypeptide is then assayed for binding to CD3 and CD4 in an ELISA assay. Microtitration plates are separately coated with CD3 or CD4 each at 0.1 ug/well in 0.1 M Tris-HCl, pH 9.2. After coating, the wells are blocked with 1% BSA in PBS. 100 ul of the anti-CD3 $V_H/V_L/C_\kappa$ and anti-CD4 $V_H/V_L/C_\lambda$ polypeptides are separately added to the substrate-coated wells to allow the antigen-binding polypeptides to bind to the substrate. The plates are maintained for 18 hours at 4° C. The plates are then washed with PBS and goat anti-human kappa chain alkaline phosphatase conjugate or goat anti-human lambda alkaline phosphatase conjugate was added (0.1 ml diluted 1:1000 in PBS containing 0.1% BSA). The plates are maintained for 2 hours at room temperature. The plates are then washed in PBS and substrate added (0.1 ml, 1 mg/ml p-nitrophenylphosphate in 0.1 M Tris-HCl at pH 9.5, containing 50 mM MgCl$_2$). After incubation at 37° C. for signal development, the optical densities at 400 nm are determined. Competition assays are performed with the addition of increasing amounts of the respective substrates ranging in concentration from zero up to 5 mg/well.

The results of the ELISA show that the expressed polypeptide binds to CD3 and to CD4 in a similar profile to that of the original OKT3 and OKT4 monoclonal antibodies, respectively.

The foregoing is intended as illustrative of the present invention but not limiting. Numerous variations and modifications can be effected without departing from the true spirit and scope of the invention.

---

What is claimed is:

1. A composition comprising a bivalent single chain polypeptide having an amino acid residue sequence according to the formula:

Fv—X—Fv, wherein Fv is an antigen binding site having an immunoglobulin variable heavy and light chain domain selected from the group consisting of $V_H/V_L$ and $V_L/V_H$, and X is an immunoglobulin constant domain.

2. The composition of claim 1 wherein said antigen binding sites specifically bind the same or different antigens.

3. The composition of claim 1 wherein said immunoglobulin constant domain is selected from the group consisting of $C_H$ and $C_L$.

4. The composition of claim 3 wherein said $C_L$ is selected from the group consisting of $C_\kappa$ and $C_\lambda$.

5. The composition of claim 1 wherein said immunoglobulin constant domain is a heavy chain constant domain ($C_H$) having a cysteine residue capable of forming at least one disulfide bridge, and said composition comprises two bivalent polypeptides covalently linked by said disulfide bride according to the formula:

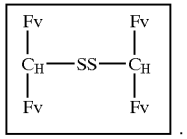

6. The composition of claim 1 wherein said immunoglobulin constant domain is an immunoglobulin light chain constant domain ($C_L$) having a cysteine residue capable of forming a disulfide bridge, and said composition contains two bivalent polypeptides covalently linked by said disulfide bridge according to the formula:

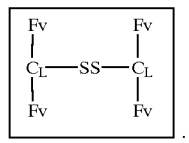

7. The composition of claim 6 wherein said $C_L$ is selected from the group consisting of $C_\kappa$ and $C_\lambda$.

8. The composition of claim 6 wherein said $C_L$ include $C_\kappa$ and $C_\lambda$.

9. The composition of claim 8 wherein one bivalent polypeptide is $C_\kappa$ and one bivalent polypeptide is $C_\lambda$.

* * * * *